(12) United States Patent
Jablonski et al.

(10) Patent No.: US 8,063,075 B2
(45) Date of Patent: *Nov. 22, 2011

(54) PYRROLIDINE ETHER DERIVATIVES AS NK3 RECEPTOR ANTAGONISTS

(75) Inventors: Philippe Jablonski, Steinbrunn-le-Haut (FR); Kenichi Kawasaki, Fujisawa (JP); Henner Knust, Rheinfelden (DE); Anja Limberg, Basel (CH); Matthias Nettekoven, Grenzach-Wyhlen (DE); Hasane Ratni, Habsheim (FR); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 205 days.

This patent is subject to a terminal disclaimer.

(21) Appl. No.: 12/476,267

(22) Filed: Jun. 2, 2009

(65) Prior Publication Data

US 2009/0306043 A1 Dec. 10, 2009

(30) Foreign Application Priority Data

Jun. 10, 2008 (EP) ..................... 08157952

(51) Int. Cl.
*A61K 31/40* (2006.01)
*A61K 31/44* (2006.01)
*C07D 207/04* (2006.01)
*C07D 401/06* (2006.01)

(52) U.S. Cl. ........ 514/340; 548/530; 548/539; 546/193; 546/276.4; 514/423; 514/318

(58) Field of Classification Search ............ 548/530, 548/539; 546/184, 193, 268.1, 276.4; 514/315, 514/318, 336, 340, 408, 423
See application file for complete search history.

(56) References Cited

U.S. PATENT DOCUMENTS

| | | | |
|---|---|---|---|
| 7,812,021 B2 * | 10/2010 | Jablonski et al. ........ | 514/235.5 |
| 2005/0065210 A1 | 3/2005 | Ackermann et al. | |
| 2006/0020011 A1 | 1/2006 | Wu et al. | |

FOREIGN PATENT DOCUMENTS
JP 2006/298909 11/2006
WO WO 2006/016167 2/2006

OTHER PUBLICATIONS

Tooney et al., Neurosci. Letters, 2000, 283, pp. 185-188.
Giardina et al., Exp. Opin. Ther. Patents, 2000, vol. 10, pp. 939-960.
Jung et al., Neuroscience, 1996, vol. 74, pp. 403-414.
Marco et al., Neuropeptides, 1998, vol. 32, pp. 481-488.
Kamali et al., Current Opinion in Investigational Drugs, 2001 vol. 2(7) pp. 950-956.
Belyk et al, Tet. Lett. 2004, vol. 45(16) pp. 3265-3268.
Albert et al., Exp. Opinion on Therapeutics Patents vol. 16(7) pp. 925-937 (2006).
Young, et al., Bioorganic & Med. Chem. Letters vol. 17(19) pp. 5310-5315 (2007).

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention relates to compounds of formula I

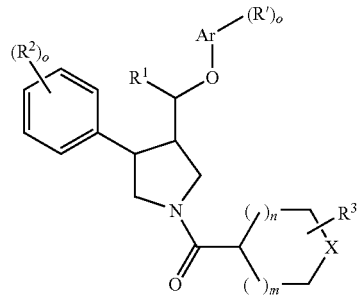

wherein $R^1$, $R^2$, $R^3$, R', Ar, m, n, and o are as defined herein. The invention also relates to pharmaceutical compositions containing compounds of formula I and methods for the manufacture of such compounds and compositions. Compounds of the invention are high potential NK-3 receptor antagonists for the treatment of depression, pain, psychosis, Parkinson's disease, schizophrenia, anxiety and attention deficit hyperactivity disorder (ADHD).

11 Claims, No Drawings

PYRROLIDINE ETHER DERIVATIVES AS NK3 RECEPTOR ANTAGONISTS

PRIORITY TO RELATED APPLICATION(S)

This application claims the benefit of European Patent Application No. 08157952.6, filed Jun. 10, 2008, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.).

SUMMARY OF THE INVENTION

The present invention provides compounds of formula I

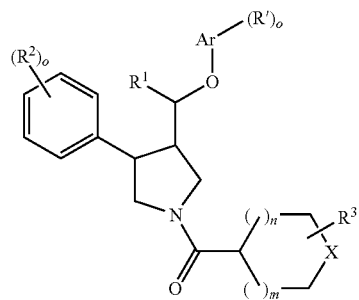

wherein $R^1$ is hydrogen or lower alkyl;

each $R^2$ is independently halogen, CN, lower alkyl, or lower alkyl substituted by halogen;

Ar is aryl or heteroaryl;

R' is hydrogen, lower alkyl, halogen, cyano or lower alkyl substituted by halogen;

$R^3$ is hydrogen, lower alkyl or hydroxy;

X is —CH($R^4$)—, —N($R^{4'}$)— or —O—;

$R^4$ is hydrogen, hydroxy, =O, lower alkyl, lower alkynyl, —S(O)$_2$-lower alkyl, —C(O)-lower alkyl, —C(O)CH$_2$O-lower alkyl, —CH$_2$CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl, —NH-lower alkyl, —NRC(O)O-lower alkyl, —NRC(O)-lower alkyl or —CH$_2$O-lower alkyl;

$R^{4'}$ is hydrogen, lower alkyl, —S(O)$_2$-lower alkyl, —C(O)-lower alkyl, —C(O)CH$_2$—O-lower alkyl, —CH$_2$CN, —C(O)CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl or —CH$_2$O-lower alkyl;

R is hydrogen or lower alkyl; or

R³ and R⁴ together with the carbon atoms to which they are attached form a five or six-membered non aromatic ring or R³ and R⁴' together with the nitrogen and carbon atoms to which they are attached form a five or six-membered non aromatic ring;

n is 0 or 1;

m is 0, 1, or 2 when n is 0; or m is 0 or 1 when n is 1; and o is 0, 1, 2 or 3;

or pharmaceutically active salts, racemic mixtures, enantiomers, optical isomers or tautomeric forms thereof.

The invention includes all sterioisomeric forms, including individual diastereoisomers and enantiomers of the compound of formula I as well as racemic and non-racemic mixtures thereof. The invention also includes pharmaceutical compositions containing compounds of formula and methods for the manufacture of the compounds and compositions of the invention.

The present compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —CF₃, —CHF₂, —CH₂F, —CH₂CF₃, —CH₂CH₂CF₃, —CH₂CF₂CF₃ and the like. Preferred lower alkyl substituted by halogen groups are groups having 1-4 carbon atoms.

The term "lower alkynyl" denotes a straight- or branched-chain hydrocarbon group containing from 2-8 carbon atoms and at least one triple bond, for example, ethynyl, propynyl, n-butynyl, i-butynyl, and the like. Preferred lower alkynyl groups are groups with 2-4 carbon atoms.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclpentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom selected from N, O and S, for example quinoxalinyl, dihydroisoquinolinyl, pyrazinyl, pyrazolyl, pyridinyl, pyridyl, pyrimidinyl, oxadiazolyl, triazolyl, tetrazolyl, thiazolyl, thiadiazolyl, thienyl, furyl, imidazolyl, or benzofuranyl. Preferred heteroaryl group is pyridinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of the present invention are compounds of formula I

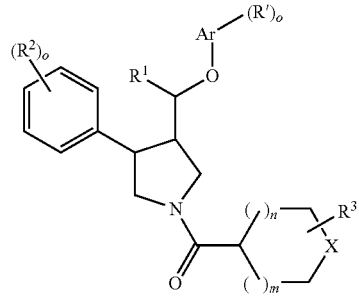

wherein

R¹ is lower alkyl;

each R² is independently halogen or CN;

Ar is heteroaryl;

R' is halogen, cyano or lower alkyl substituted by halogen;

R³ is hydrogen or hydroxy;

X is —CH(R⁴)—, —N(R⁴')— or —O—;

R⁴ is hydrogen, hydroxy, =O, lower alkynyl, —S(O)₂-lower alkyl, —NH-lower alkyl, —NRC(O)O-lower alkyl, —NRC(O)-lower alkyl or —CH₂O-lower alkyl;

R⁴' is hydrogen, lower alkyl, —S(O)₂-lower alkyl, —C(O)-lower alkyl, —C(O)CH₂—O-lower alkyl, —CH₂CN, —C(O)CH₂CN, —C(O)-cycloalkyl wherein the cycloalkyl group is optionally substituted by cyano, lower alkyl, one or two halogen atoms, =O or amino, or is —C(O)O-lower alkyl;

R is hydrogen or lower alkyl;

n is 0 or 1;

m is 0, 1, or 2 when n is 0; or m is 0 or 1 when n is 1; and o is 1 or 2;

or pharmaceutically active salts, racemic mixtures, enantiomers, optical isomers or tautomeric forms thereof.

Compounds of formula I, wherein Ar is heteroaryl, are preferred. Especially preferred are compounds of formula I, wherein Ar is pyridinyl.

Compounds of formula I, wherein X is —CH(R⁴)—, are preferred. For example the following compounds:

{4-[(3RS,4SR)-3-[(SR)-1-(5-chloro-pyridin-2-yloxy)-ethyl]-4-(3,4-dichloro-phenyl)-pyrrolidine-1-carbonyl]-cycloheyl}-carbamic acid methyl ester;

[(3RS,4SR)-3-[(SR)-1-(5-chloro-pyridin-2-yloxy)-ethyl]-4-(3,4-dichloro-phenyl)-pyrrolidin-1-yl]-(4-methoxymethyl-cyclohexyl)-methanone;

[(3RS,4SR)-3-[(SR)-1-(5-chloro-pyridin-2-yloxy)-ethyl]-4-(3,4-dichloro-phenyl)-pyrrolidin-1-yl]-(4-ethynyl-cyclohexyl)-methanone;
4-[(3RS,4SR)-3-[(SR)-1-(5-chloro-pyridin-2-yloxy)-ethyl]-4-(3,4-dichloro-phenyl)-pyrrolidine-1-carbonyl]-cyclohexanone;
{4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-methyl-carbamic acid tert-butyl ester;
{4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-carbamic acid tert-butyl ester; and
N-{4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-N-methyl-acetamide.

Compounds of formula I, wherein X is —N($R^{4'}$)—, are preferred. For example the following compounds:
1-{4-[(3RS,4SR)-3-[(SR)-1-(5-chloro-pyridin-2-yloxy)-ethyl]-4-(3,4-dichloro-phenyl)-pyrrolidine-1-carbonyl]-piperidin-1-yl}-ethanone;
6-{(SR)-1-[(3RS,4SR)-1-(1-acetyl-piperidine-4-carbonyl)-4-(3,4-dichloro-phenyl)-pyrrolidin-1-yl]-(1-cyclobutanecarbonyl-piperidin-4-yl)-methanone;
[(3RS,4SR)-3-[(SR)-1-(5-chloro-pyridin-2-yloxy)-ethyl]-4-(3,4-dichloro-phenyl)-pyrrolidin-3-yl]-ethoxy}-nicotinonitrile;
[(3RS,4SR)-3-[(SR)-1-(5-chloro-pyridin-2-yloxy)-ethyl]-4-(3,4-dichloro-phenyl)-pyrrolidin-1-yl]-(1-isobutyl-piperidin-4-yl)-methanone;
4-[(3RS,4SR)-3-[(SR)-1-(5-cyano-pyridin-2-yloxy)-ethyl]-4-(3,4-dichloro-phenyl)-pyrrolidine-1-carbonyl]-piperidine-1-carboxylic acid tert-butyl ester;
6-{(SR)-1-[(3RS,4SR)-1-(1-cyclopropanecarbonyl-piperidine-4-carbonyl)-4-(3,4-dichloro-phenyl)-pyrrolidin-3-yl]-ethoxy}-nicotinonitrile;
6-((SR)-1-{(3RS,4SR)-4-(3,4-dichloro-phenyl)-1-[1-(1-methyl-cyclopropanecarbonyl)-piperidine-4-carbonyl]-pyrrolidin-3-yl}-ethoxy)-nicotinonitrile;
6-{(SR)-1-[(3RS,4SR)-1-[1-(1-amino-cyclopropanecarbonyl)-piperidine-4-carbonyl]-4-(3,4-dichloro-phenyl)-pyrrolidin-3-yl]-ethoxy}-nicotinonitrile;
6-{(SR)-1-[(3RS,4SR)-1-(1-cyclobutanecarbonyl-piperidine-4-carbonyl)-4-(3,4-dichloro-phenyl)-pyrrolidin-3-yl]-ethoxy}-nicotinonitrile;
6-((SR)-1-{(3RS,4SR)-4-(3,4-dichloro-phenyl)-1-[1-(3-oxo-cyclobutanecarbonyl)-piperidine-4-carbonyl]-pyrrolidin-3-yl}-ethoxy)-nicotinonitrile;
6-{(SR)-1-[(3RS,4SR)-4-(3,4-dichloro-phenyl)-1-(1-propionyl-piperidine-4-carbonyl)-pyrrolidin-3-yl]-ethoxy}-nicotinonitrile;
6-{(SR)-1-[(3RS,4SR)-1-[1-(2-cyano-acetyl)-piperidine-4-carbonyl]-4-(3,4-dichloro-phenyl)-pyrrolidin-3-yl]-ethoxy}-nicotinonitrile;
6-((SR)-1-{(3RS,4SR)-4-(3,4-dichloro-phenyl)-1-[1-(2-methoxy-acetyl)-piperidine-4-carbonyl]-pyrrolidin-3-yl}-ethoxy)-nicotinonitrile;
1-(4-{(3SR,4RS)-3-(3,4-dichloro-phenyl)-4-[(SR)-1-(5-trifluoromethyl-pyridin-2-yloxy)-ethyl]-pyrrolidine-1-carbonyl}-piperidin-1-yl)-ethanone;
6-((SR)-1-{(3RS,4SR)-4-(3,4-dichloro-phenyl)-1-[1-(1-methyl-cyclopropanecarbonyl)-piperidine-4-carbonyl]-pyrrolidin-3-yl}-ethoxy)-nicotinonitrile;
[(3RS,4SR)-3-[(SR)-1-(5-chloro-pyridin-2-yloxy)-ethyl]-4-(2,4-difluoro-phenyl)-pyrrolidin-1-yl]-[1-(1-methyl-cyclopropanecarbonyl)-piperidin-4-yl]-methanone;
{(3S,4R)-3-(4-chloro-phenyl)-4-[(S)-1-(5-chloro-pyridin-2-yloxy)-ethyl]-pyrrolidin-1-yl}-[1-(1-methyl-cyclopropanecarbonyl)-piperidin-4-yl]-methanone; and
{(3S,4R)-3-(4-chloro-3-fluoro-phenyl)-4-[(S)-1-(5-chloro-pyridin-2-yloxy)-ethyl]-pyrrolidin-1-yl}-[1-(1-methyl-cyclopropanecarbonyl)-piperidin-4-yl]-methanone.

Compounds of formula I, wherein X is —O—, are also preferred, for example the following compound:
{(3SR,4RS)-3-(3,4-Dichloro-phenyl)-4-[(SR)-1-(5-trifluoromethyl-pyridin-2-yloxy)-ethyl]-pyrrolidin-1-yl}-(tetrahydro-pyran-4-yl)-methanone.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process described below, which process comprises a) coupling a compound of formula VII

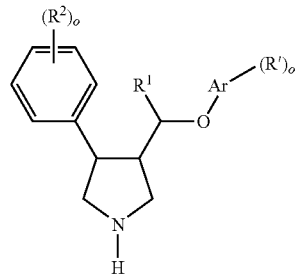

VII with a suitable acid chloride or carboxylic acid of formula

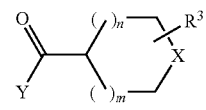

wherein Y is halogen or hydroxy,
to obtain a compound of formula I

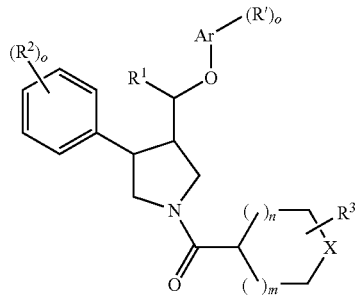

wherein the substituents $R^1$, $R^2$, $R^1$, $R^3$, X and Ar and the definitions o, n and m are described above, or
b) reacting a compound of formula VIII

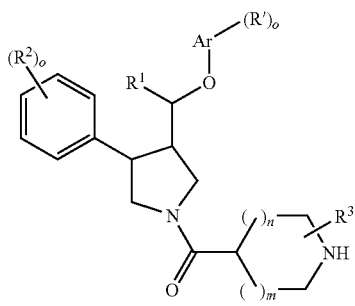

with a compound of formula $$R^{4'}-Z$$

wherein Z is halogen,
to obtain a compound of formula

I

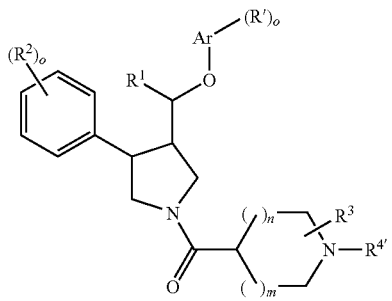

wherein the substituents $R^1$, $R^2$, $R^3$, $R^{4'}$, R', Ar and the definitions o, n and m are described above, or,
if desired, converting the compounds obtained into pharmaceutically acceptable acid addition salts.

The preparation of compounds of formula I is further described in more detail in schemes I-V and in examples 1-53.

Abbreviations:
$CH_2Cl_2$: dichloromethane;
DMAP: dimethylaminopyridine;
HOBt: 1-hydroxy-benzotriazol hydrat;
EDC: 1-(3-dimethylaminopropyl)-3-ethylcarbodiimide hydrochloride;
$Et_3N$: triethylamine;
EtOAc: ethyl acetate;
H: hexane;
RT: room temperature;
$PPh_3$: triphenylphosphine;
DBAD: di-tert-butyl azodicarboxylate

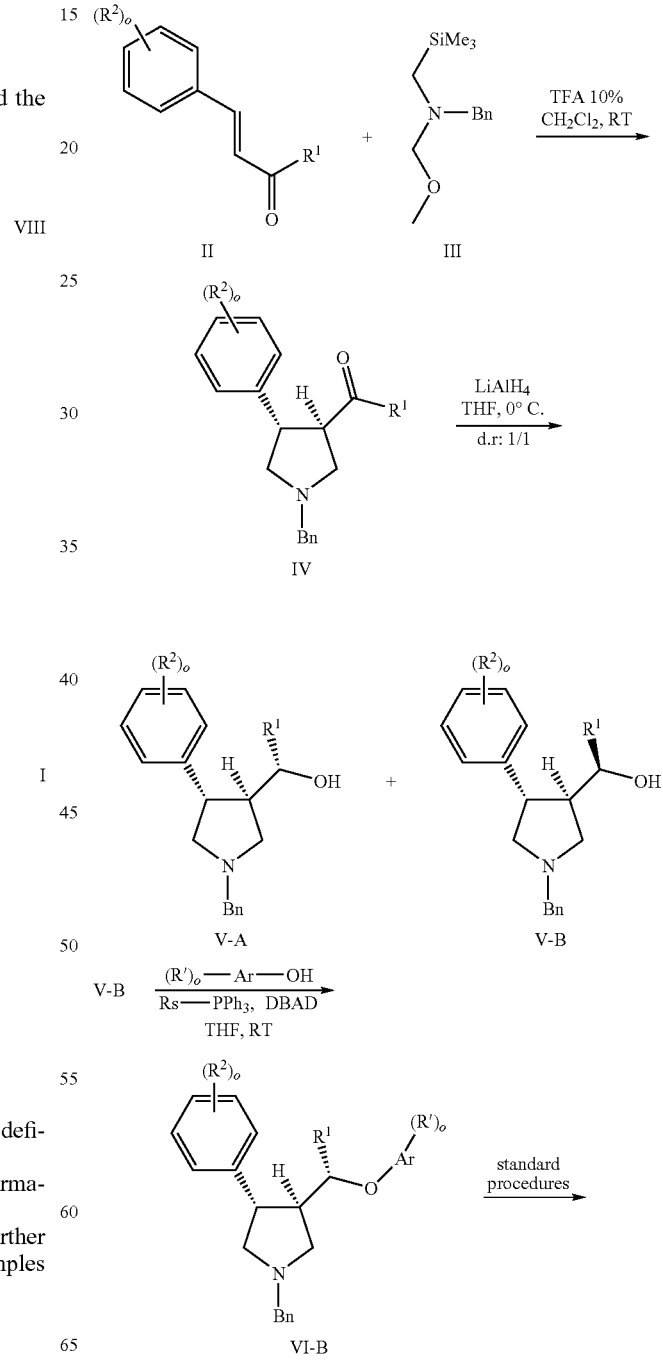

General Scheme I

-continued

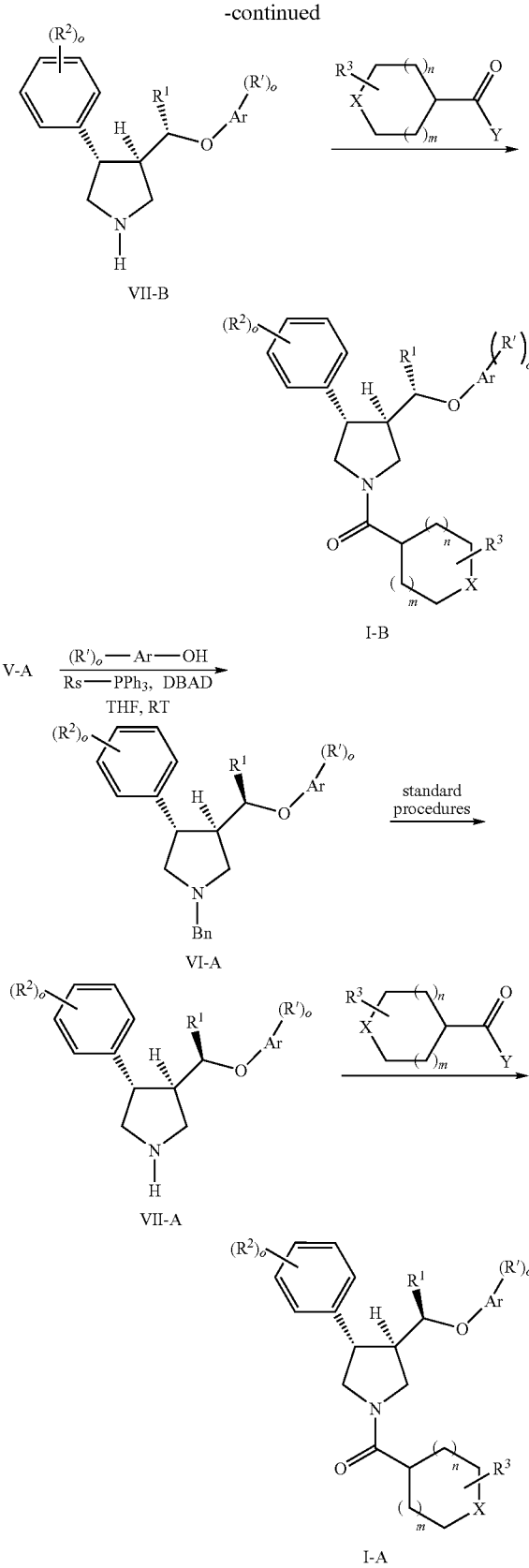

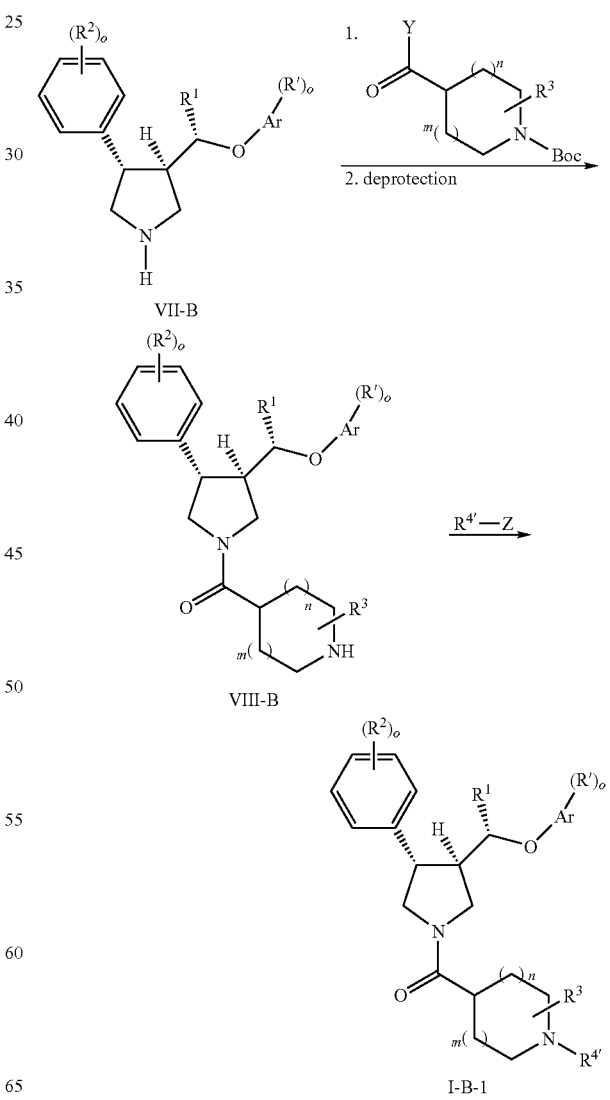

The 3,4-disubstituted pyrrolidines IV are prepared via a stereo specific 1,3-dipolar cycloaddition between substituted (E)-4-phenyl-but-3-en-2-one derivative II and the azomethine ylide generated in situ from the N-(methoxymethyl)-N-(phenylmethyl)-N-(trimethylsilyl)methylamine III in the presence of a catalytic amount of acid, such as TFA. Reduction of the acetyl moiety using standard conditions for example LiAlH$_4$ yields the two diasteroisomers V-A and V-B which are subsequently separated by column chromatography. Each of the diastereoisomers is then separately converted to the final derivatives I-A and I-B in the same manner. For instance V-B is subjected to a standard Mitsunobu reaction with for example a phenol, pyridin-ol, pyrimidin-ol to give the aryl-ether VI-B. Selective N-debenzylation is then carried out using several known procedures which are compatible with the substitution patterns of the aromatic rings to afford VII-B. Final derivatives I-B are prepared via a coupling with a suitable acid chloride or carboxylic acid using known methods, wherein Y is hydroxy or halogen, R$^1$ a methyl moiety and the other definitions are as described above.

wherein Y is halogen or hydroxy, R$^1$ a lower alkyl and the other definitions are as above.

wherein Y is hydroxy or halogen, Z is halogen and the other definitions are as described above.

Alternatively the pyrrolidine VII-B can undergo a coupling with a carboxylic acid derivative which after selective Boc deprotection generated the intermediate VIII-B. Final derivatives I-B-1 are prepared via a coupling with $R^{4'}$—Y using well known reactions and procedures.

In the same manner, the diastereomer VII-A can be converted to final derivatives I-A.

General scheme III

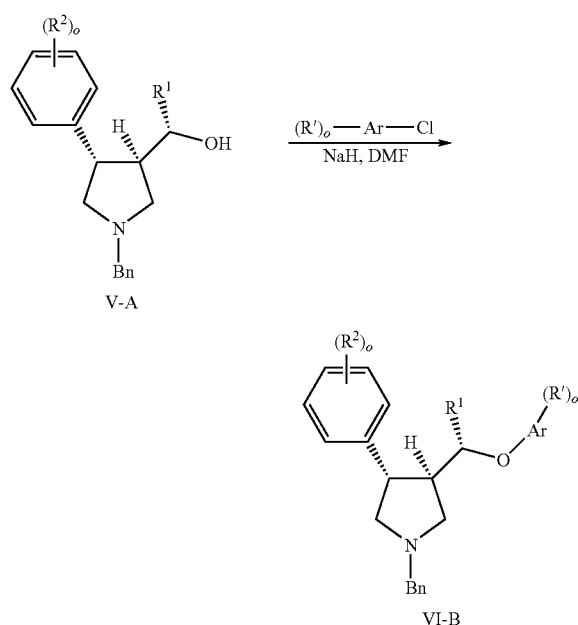

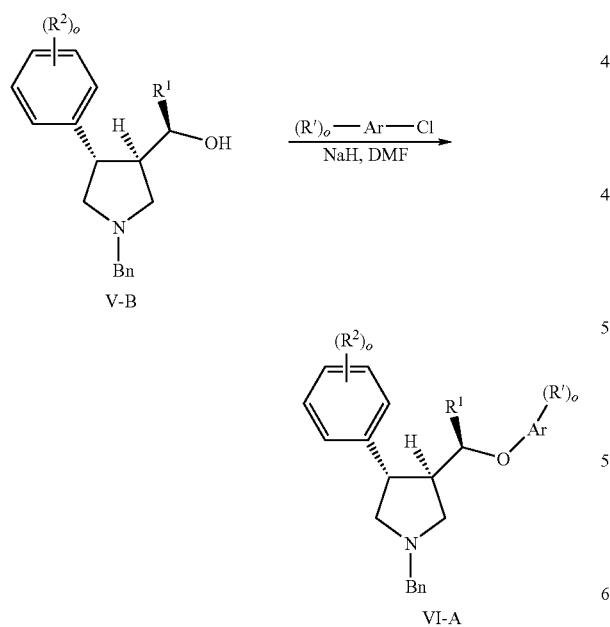

Alternatively to the Mitsunobu reaction shown scheme I, derivatives V-A and V-B can used in a nucleophilic aromatic substitution reaction when the Ar moiety is a o-pyridinyl or a o-pyrimidinyl to yield respectively VI-B and VI-A.

General Scheme IV

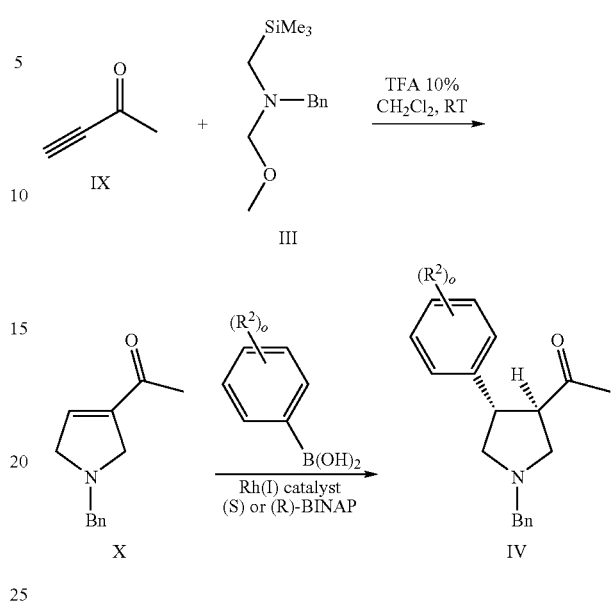

An alternative method for the preparation of intermediates IV (with $R^1$ is Me) is highlighted scheme 4. A 1,3-dipolar cycloaddition between the commercially available but-3-yn-2-one IX and the azomethine ylide generated in situ from the N-(methoxymethyl)-N-(phenylmethyl)-N-(trimethylsilyl)methylamine III in the presence of a catalytic amount of acid, such as TFA afforded the dihydropyrrole derivative X. A 1,4-addition of a boronic acid catalysed by a Rh(I) catalyst such as the Rhacetylacetonatbis(ethylene) in a presence of a chiral phosphine ligand such as the (R) or (S)-BINAP afforded the optically enriched disubstituted pyrrolidine IV. Similar Rh-catalysed asymmetric 1,4-arylation have been reported earlier (*Tet. Lett.*, 2004, 45(16), 3265)

General scheme V

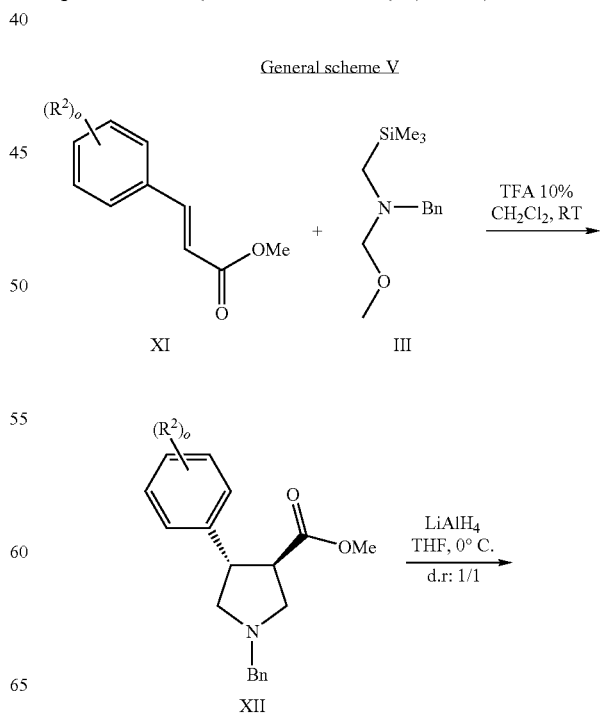

-continued

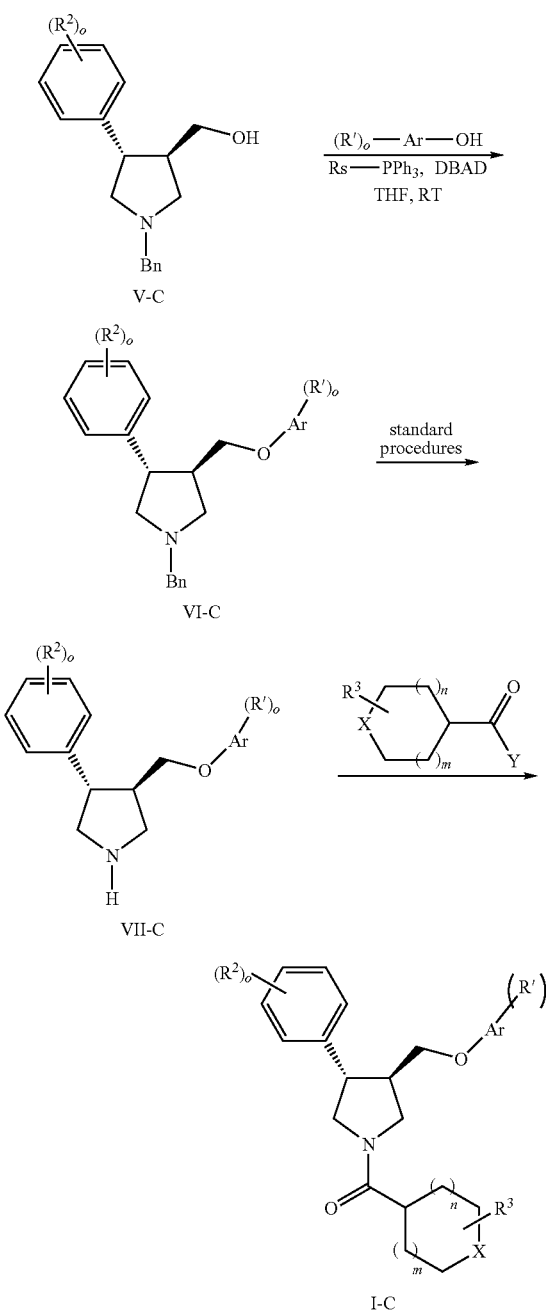

The derivatives of the type I-C with $R^1$ equal H where prepared via the following route (scheme 5). The 3,4-disubstituted pyrrolidines XII were prepared via a stereo specific 1,3-dipolar cycloaddition between the (E)-3-substituted phenyl-acrylic acid ethyl ester derivatives XI and the azomethine ylide generated in situ from the N-(methoxymethyl)-N-(phenylmethyl)-N-(trimethylsilyl)methylamine III in the presence of a catalytic amount of acid, such as TFA. Reduction of the ester moiety using standard conditions for example $LiAlH_4$ yielded the primary alcohol V-C. Standard Mitsunobu reaction with for example a phenol, pyridin-ol, pyrimidin-ol gave the aryl-ether VI-C. Selective N-debenzylation was then carried out using several known procedures which are compatible with the substitution patterns of the aromatic rings to afford VII-C. Final derivatives I-C were obtained via a coupling with a suitable acid chloride or carboxylic acid using known methods.

EXPERIMENTAL PROCEDURES

As mentioned earlier, the compounds of formula I and their pharmaceutically usable addition salts possess valuable pharmacological properties. Compounds of the present invention are antagonists of neurokinin 3 (NK-3) receptors.

Experimental Procedure

The compounds were investigated in accordance with the tests given hereinafter.
[$^3$H]SR142801 Competition Binding Assay
hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM $MnCl_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S. A., Zürich, Switzerland) and shaking for 1 h. Inhibition curves were fitted according to the Hill equation: $y=100/(1+(x/IC_{50})^{n_H})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

Results of some compounds of the invention are shown in the following Table 1.

TABLE 1

| Example | Data [µM] |
|---------|-----------|
| 1 | 0.0047 |
| 2 | 0.0076 |
| 3 | 0.0012 |
| 5 | 0.0095 |
| 6 | 0.0058 |
| 10 | 0.009 |
| 11 | 0.0061 |
| 12 | 0.0092 |
| 13 | 0.0044 |
| 14 | 0.0049 |
| 17 | 0.0046 |

TABLE 1-continued

| Example | Data [μM] |
|---------|-----------|
| 19 | 0.0077 |
| 20 | 0.0026 |
| 21 | 0.0021 |
| 22 | 0.0036 |
| 23 | 0.0075 |
| 24 | 0.0036 |
| 42 | 0.0028 |
| 43 | 0.007 |
| 45 | 0.004 |
| 46 | 0.0018 |
| 47 | 0.0019 |
| 48 | 0.0074 |
| 52 | 0.001 |
| 53 | 0.0008 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers.

Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention without limiting it. All temperatures are given in degrees Celsius.

General Procedure I: Amid Coupling (Pyrrolidine VII and Carboxylic Acid)

To a stirred solution of a carboxylic acid derivative (commercially available or known in the literature) (1 mmol) in 10 mL of $CH_2Cl_2$ was added (1.3 mmol) of EDC, (1.3 mmol) of HOBt and $Et_3N$ (1.3 mmol). After one hour at RT, was added a pyrrolidine intermediate of general formula (VII). The mixture was stirred at RT over night and then poured onto water and extracted with $CH_2Cl_2$. The combined organic phases were dried over $Na_2SO_4$ and concentrated under vacuo. Flash chromatography or preparative HPLC afforded the title compound.

General Procedure II: Coupling Between a Compound of Formula VII or VIII with an Acid Chloride, Chloroformate or Sulfonyl Chloride A solution of the pyrrolidine (1 mmol) of formula (VII) in CH$_2$Cl$_2$ (10 mL) was treated with Et$_3$N (1.2 mmol) and an acid chloride, chloroformate or sulfonylchlorid (1.2 mmol) and stirred at RT overnight. Purification by preparative HPLC yielded the title compound.

Pyrrolidine Intermediates of Formula VII-B

Pyrrolidine VII-B-1

5-Chloro-2-{(SR)-1-[(3RS,4SR)-4-(3,4-dichloro-phenyl)-pyrrolidin-3-yl]-ethoxy}-pyridine

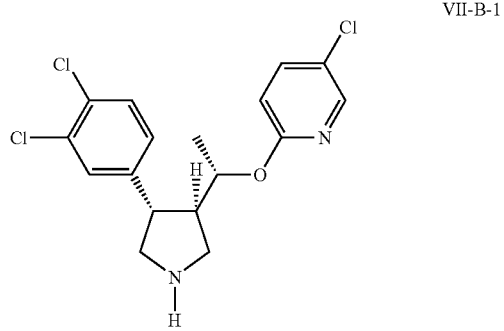

VII-B-1 a) 1-[(3RS,4SR)-1-Benzyl-4-(3,4-dichloro-phenyl)-pyrrolidin-3-yl]-ethanone (IV-1)

A solution of N-(methoxymethyl)-N-(phenylmethyl)-N-(trimethylsilyl)methylamine (32.78 g, 0.138 mol) in CH$_2$Cl$_2$ (50 mL) was added dropwise, over a 30 minutes period, to a stirred solution of (E)-4-(3,4-dichloro-phenyl)-but-3-en-2-one (19.80 g, 0.092 mol) and trifluoroacetic acid (1.05 mL, 0.009 mol) in CH$_2$Cl$_2$ (100 mL) at 0° C. The ice bath was removed, and the solution was stirred at 25° C. for an additional 48 h. It was then concentrated and purification by flash chromatography (SiO$_2$, CH$_2$Cl$_2$/MeOH 98:2) afforded 28.3 g (88%) of the title compound as a yellow oil. ES-MS m/e: 348.2 (M+H$^+$).

b) (SR)-1-[(3RS,4SR)-1-Benzyl-4-(3,4-dichloro-phenyl)-pyrrolidin-3-yl]-ethanol (V-A-1) and (RS)-1-[(3RS,4SR)-1-Benzyl-4-(3,4-dichloro-phenyl)-pyrrolidin-3-yl]-ethanol (V-B-1)

To a solution of 1-[(3SR,4RS)-1-benzyl-4-(3,4-dichloro-phenyl)-pyrrolidin-3-yl]-ethanone (IV-1) (14.90 g, 0.043 mol) in THF (300 mL) at 0° C. were added portion wise LiAlH$_4$ (2.05 g, 0.051 mol). Stirring was continued for one hour, and the reaction mixture was carefully quenched by addition of aq. NH$_4$Cl, concentrated under vacuo and the product extracted with EtOAC. The combined organic phases were dried on Na$_2$SO$_4$ and concentrated under vacuo. The two diastereoisomeres were separated by column chromatography (SiO$_2$, EtOAc/H, 1:1) to yield (RS)-1-[(3RS,4SR)-4-(3,4-dichloro-phenyl)-pyrrolidin-3-yl]-ethanol (V-B-1) 4.69 g (31%) as a white solid ES-MS m/e: 350.2 (M+H$^+$) and (SR)-1-[(3RS,4SR)-4-(3,4-dichloro-phenyl)-pyrrolidin-3-yl]-ethanol (V-A-1) 5.30 g (35%) as a white solid ES-MS m/e: 350.2 (M+H$^+$).

c) 2-{(SR)-1-[(3RS,4SR)-1-Benzyl-4-(3,4-dichloro-phenyl)-pyrrolidin-3-yl]-ethoxy-}-5-chloro-pyridine To a suspension of PPh$_3$ (PPh$_3$ polymer bound, 3 mmol PPh$_3$/g resin) (3.14 g, 9.4 mmol) in THF (70 mL) at 0° C. were added 5-chloro-pyridin-2-ol (0.832 g, 6.42 mmol) and then DBAD (1.578 g, 6.85 mmol). After 5 minutes was added (RS)-1-[(3RS,4SR)-4-(3,4-dichloro-phenyl)-pyrrolidin-3-yl]-ethanol (V-B-1) (1.50 g, 4.28 mmol). The reaction mixture was stirred over night at RT, filtered on celite and concentrated under vacuo. Extraction with EtOAc/aq.NaOH 1M, followed by column chromatography (SiO$_2$, EtOAc/H, 1:6) yielded 1.71 g (87%) of the title compound as a colorless oil. ES-MS m/e: 461.2 (M+H$^+$).

d) 5-Chloro-2-{(SR)-1-[(3RS,4SR)-4-(3,4-dichloro-phenyl)-pyrrolidin-3-yl]-ethoxy}-pyridine (VII-B-1)

To a solution of 2-{(SR)-1-[(3RS,4SR)-1-benzyl-4-(3,4-dichloro-phenyl)-pyrrolidin-3-yl]-ethoxy}-5-chloro-pyridine (1.71 g (3.71 mmol) dissolved in CH$_3$CN (50 mL) was added 0.75 mL (5.57 mmol) of 2,2,2-trichloroethyl chloroformate and stirring was continued for 4 hours at RT. Volatiles were removed under vacuo, and the crude was dissolved in AcOH (30 mL) before a total of 1.0 g of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.74 g (54%) of the title compound as a colorless oil. ES-MS m/e: 373.1 (M+H$^+$).

Pyrrolidine VII-B-2

6-{(SR)-1-[(3RS,4SR)-4-(3,4-Dichloro-phenyl)-pyrrolidin-3-yl]-ethoxy}-nicotinonitrile

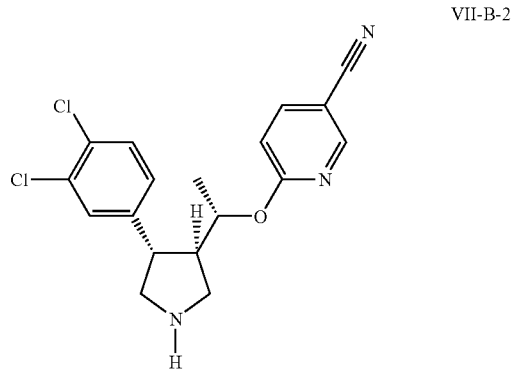

VII-B-2 a) 6-{(SR)-1-[(3RS,4SR)-1-Benzyl-4-(3,4-dichloro-phenyl)-pyrrolidin-3-yl]-ethoxy}-nicotinonitrile To a suspension of PPh$_3$ (PPh$_3$ polymer bound, 3 mmol PPh$_3$/g resin) (1.97 g) in THF (300 mL) at 0° C. were added 6-hydroxy-nicotinonitrile (0.61 g, 5.1 mmol) and then DBAD (1.10 g). After 5 minutes was added (RS)-1-[(3RS,4SR)-4-(3,4-dichloro-phenyl)-pyrrolidin-3-yl]-ethanol (V-B-1) (1.20 g, 3.4 mmol, described herein above). The reaction mixture was stirred over night at RT, filtered on celite and concentrated under vacuo. Extraction with EtOAc/aq.NaOH 1M, followed by column chromatography (SiO$_2$, EtOAc/H, 1:4) yielded 1.02 g (66%) of the title compound as a colorless oil. ES-MS m/e: 452.0 (M+H$^+$).

b) 6-{(SR)-1-[(3RS,4SR)-4-(3,4-Dichloro-phenyl)-pyrrolidin-3-yl]-ethoxy}-nicotinonitrile (VII-B-2)

To a solution of 6-{(SR)-1-[(3RS,4SR)-1-benzyl-4-(3,4-dichloro-phenyl)-pyrrolidin-3-yl]-ethoxy}-nicotinonitrile 0.75 g (1.70 mmol) dissolved in CH$_3$CN (50 mL) was added 0.56 mL (4.14 mmol) of 2,2,2-trichloroethyl chloroformate and stirring was continued for 4 hours at RT. Volatiles were removed under vacuo, and the crude was dissolved in AcOH (30 mL) before a total of 0.45 g of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.36 g (60%) of the title compound as a colorless oil. ES-MS m/e: 362.3 (M+H$^+$).

Pyrrolidine VII-B-3

2-{(SR)-1-[(3RS,4SR)-4-(3,4-Dichloro-phenyl)-pyrrolidin-3-yl]-ethoxy}-5-trifluoromethyl-pyridine

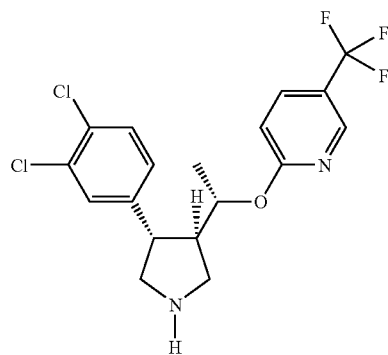

VII-B-3 a) 2-{(SR)-1-[(3RS,4SR)-1-Benzyl-4-(3,4-dichloro-phenyl)-pyrrolidin-3-yl]-ethoxy}-5-trifluoromethyl-pyridine To a suspension of PPh$_3$ (PPh$_3$ polymer bound, 3 mmol PPh$_3$/g resin) (0.77 g) in THF (25 mL) at 0° C. were added 5-trifluoromethyl-pyridin-2-ol (0.28 g, 1.75 mmol) and then DBAD (0.43 g). After 5 minutes was added (RS)-1-[(3RS,4SR)-4-(3,4-dichloro-phenyl)-pyrrolidin-3-yl]-ethanol (V-B-1) (0.41 g, 1.17 mmol, described herein above). The reaction mixture was stirred over night at RT, filtered on celite and concentrated under vacuo. Extraction with EtOAc/aq.NaOH 1M, followed by column chromatography (SiO$_2$, EtOAc/H, 1:4) yielded 0.45 g (78%) of the title compound as a colorless oil. ES-MS m/e: 495.8 (M+H$^+$).

b) 2-{(SR)-1-[(3RS,4SR)-4-(3,4-Dichloro-phenyl)-pyrrolidin-3-yl]-ethoxy}-5-trifluoromethyl-pyridine (VII-B-3)

To a solution of 2-{(SR)-1-[(3RS,4SR)-1-benzyl-4-(3,4-dichloro-phenyl)-pyrrolidin-3-yl]-ethoxy}-5-trifluoromethyl-pyridine 0.45 g (0.91 mmol) dissolved in toluene (5 mL) were added 0.30 mL (2.7 mmol) of 1-chloroethyl chloroformate and 0.46 mL of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 0.32 g (87%) of the title compound as a light yellow oil. ES-MS m/e: 405.9 (M+H$^+$).

Pyrrolidine VII-B-4

5-Chloro-2-{(SR)-1-[(3RS,4SR)-4-(2,4-difluoro-phenyl)-pyrrolidin-3-yl]-ethoxy}-pyridine

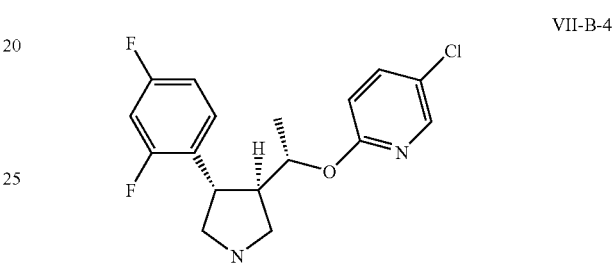

VII-B-4 a) (E)-4-(2,4-Difluoro-phenyl)-but-3-en-2-one

A two necked flask was charged with 2,4-difluorobenzaldehyde (4.0 g, 28.1 mmol) and (2-oxo-propyl)-phosphonic acid dimethyl ester (5.78 g, 33.0 mmol) and cooled down at 0° C. K$_2$CO$_3$ (7.62 g, 55.1 mmol) in H$_2$O (14 mL) was added dropwise. Stirring was continued over night at RT. The product was extracted with EtOAc, and the organic phase was dried over Na$_2$SO$_4$. Flash chromatography (SiO$_2$, Heptane/EtOAc 1:3) afforded 4.0 g (79%) of the title compound as a light yellow oil.

b) 1-[(3RS,4SR)-1-Benzyl-4-(2,4-difluoro-phenyl)-pyrrolidin-3-yl]-ethanone (IV-4)

A solution of N-(methoxymethyl)-N-(phenylmethyl)-N-(trimethylsilyl)methylamine (7.82 g, 32.9 mmol) in CH$_2$Cl$_2$ (40 mL) was added dropwise, over a 30 minutes period, to a stirred solution of (E)-4-(2,4-difluoro-phenyl)-but-3-en-2-one (4.0 g, 21.9 mmol) and trifluoroacetic acid (0.17 mL, 0.21 mmol) in CH$_2$Cl$_2$ (10 mL) at 0° C. The ice bath was removed, and the solution was stirred at 25° C. for an additional 48 h. It was then concentrated and purification by flash chromatography (SiO$_2$, CH$_2$Cl$_2$/MeOH 98:2) afforded 6.2 g (89%) of the title compound as a yellow oil. ES-MS m/e: 316.1 (M+H$^+$).

c) (RS)-1-[(3SR,4RS)-4-(2,4-Difluoro-phenyl)-pyrrolidin-3-yl]-ethanol (V-A-4) and (SR)-1-[(3SR,4RS)-4-(2,4-Dichloro-phenyl)-pyrrolidin-3-yl]-ethanol (V-B-4)

To a solution of 1-[(3RS,4SR)-1-benzyl-4-(2,4-difluoro-phenyl)-pyrrolidin-3-yl]-ethanone (IV-4) (1.87 g, 5.92 mmol) in THF (30 mL) at 0° C. were added portion wise LiAlH$_4$ (0.19 g, 5.21 mol). Stirring was continued for one hour, and the reaction mixture was carefully quenched by addition of aq. NH₄Cl, concentrated under vacuo and the product extracted with EtOAC. The combined organic phases were dried on Na₂SO₄ and concentrated under vacuo. The two diastereoisomeres were separated by column chromatography (SiO₂, EtOAc/H, 1:1) to yield (RS)-1-[(3RS,4SR)-4-(2,4-difluoro-phenyl)-pyrrolidin-3-yl]-ethanol (V-B-4) 0.72 g (38%) as a white solid ES-MS m/e: 318.1 (M+H⁺) and (SR)-1-[(3RS,4SR)-4-(2,4-difluoro-phenyl)-pyrrolidin-3-yl]-ethanol (V-A-4) 0.374 g (19%) as a white solid ES-MS m/e: 318.1 (M+H⁺).

d) 2-{(SR)-1-[(3RS,4SR)-1-Benzyl-4-(2,4-difluoro-phenyl)-pyrrolidin-3-yl]-ethoxy}-5-chloro-pyridine (VI-B-4)

To a suspension of PPh₃ (PPh₃ polymer bound, 3 mmol PPh₃/g resin) (1.27 g, 4.85 mmol) in THF (25 mL) at 0° C. were added 5-chloro-pyridin-2-ol (0.429 g, 3.31 mmol) and then DBAD (0.81 g, 3.51 mmol). After 5 minutes was added (RS)-1-[(3RS,4SR)-4-(2,4-difluoro-phenyl)-pyrrolidin-3-yl]-ethanol (V-B-4) (0.70 g, 2.20 mmol). The reaction mixture was stirred over night at RT, filtered on celite and concentrated under vacuo. Extraction with EtOAc/aq.NaOH 1M, followed by column chromatography (SiO₂, EtOAc/H, 1:6) yielded 0.69 g (73%) of the title compound as a colorless oil. ES-MS m/e: 429.2 (M+H⁺).

e) 5-Chloro-2-{(SR)-1-[(3RS,4SR)-4-(2,4-difluoro-phenyl)-pyrrolidin-3-yl]-ethoxy}-pyridine (VII-B-4)

To a solution of 2-{(SR)-1-[(3RS,4SR)-1-benzyl-4-(2,4-difluoro-phenyl)-pyrrolidin-3-yl]-ethoxy}-5-chloro-pyridine 570 mg (1.32 mmol) dissolved in toluene (12 mL) were added 0.43 mL (3.96 mmol) of 1-chloroethyl chloroformate and 0.68 mL (3.96 mmol) of Hunig's base.

The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 350 mg (78%) of the title compound as a light yellow oil. ES-MS m/e: 339.1 (M+H⁺).

Pyrrolidine VII-B-5

6-{(SR)-1-[(3RS,4SR)-4-(4-Cyano-phenyl)-pyrrolidin-3-yl]-ethoxy}-nicotinonitrile

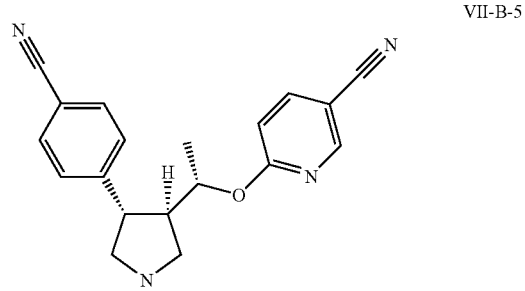

VII-B-5 a) 4-((E)-3-Oxo-but-1-enyl)-benzonitrile

A two necked flask was charged with 4-formyl-benzonitrile (20.0 g, 0.152 mol) and (2-oxo-propyl)-phosphonic acid dimethyl ester (30.4 g, 0.18 mol) and cooled down at 0° C. K₂CO₃ (42.16 g, 0.305 mol) in H₂O (45 mL) was added dropwise. Stirring was continued over night at RT. The product was extracted with EtOAc, and the organic phase was dried over Na₂SO₄. Flash chromatography (SiO₂, Heptane/EtOAc 1:1) afforded 18.7 g (72%) of the title compound as alight yellow solid.

b) 4-((3SR,4RS)-4-Acetyl-1-benzyl-pyrrolidin-3-yl)-benzonitrile (IV-5)

A solution of N-(methoxymethyl)-N-(phenylmethyl)-N-(trimethylsilyl)methylamine (22.46 g, 94.6 mmol) in CH₂Cl₂ (100 mL) was added dropwise, over a 30 minutes period, to a stirred solution of 4-((E)-3-oxo-but-1-enyl)-benzonitrile (10.8 g, 63.1 mmol) and trifluoroacetic acid (0.48 mL, 6.30 mmol) in CH₂Cl₂ (40 mL) at 0° C. The ice bath was removed, and the solution was stirred at 25° C. for an additional 48 h. It was then concentrated and purification by flash chromatography (SiO₂, EtOac/Heptane 1:1) afforded 6.3 g (33%) of the title compound as a yellow oil. ES-MS m/e: 305.1 (M+H⁺).

c) 4-[(3 SR,4RS)-1-Benzyl-4-((SR)-1-hydroxy-ethyl)-pyrrolidin-3-yl]-benzonitrile (V-A-5) and 4-[(3 SR,4RS)-1-Benzyl-4-((RS)-1-hydroxy-ethyl)-pyrrolidin-3-yl]-benzonitrile (V-B-5)

To a solution of 4-((3SR,4RS)-4-acetyl-1-benzyl-pyrrolidin-3-yl)-benzonitrile (IV-5) (IV-5) (6.30 g, 20.7 mmol) in MeOH (300 mL) at RT were added portion wise LiBH₄ (9.49 g, 0.43 mol). Stirring was continued for overnight, and the reaction mixture was carefully quenched by addition of aq. NH₄Cl, concentrated under vacuo and the product extracted with EtOAC. The combined organic phases were dried on Na₂SO₄ and concentrated under vacuo. The two diastereoisomeres were separated by column chromatography (SiO₂, EtOAc/H, 1:1) to yield 4-[(3SR,4RS)-1-benzyl-4-((RS)-1-hydroxy-ethyl)-pyrrolidin-3-yl]-benzonitrile (V-B-5) 1.35 g (21%) as a colorless oil ES-MS m/e: 307.2 (M+H⁺) and 4-[(3SR,4RS)-1-benzyl-4-((SR)-1-hydroxy-ethyl)-pyrrolidin-3-yl]-benzonitrile (V-A-5) 1.30 g (20%) as a colorless oil ES-MS m/e: 307.2 (M+H⁺).

d) 6-{(SR)-1-[(3RS,4SR)-1-Benzyl-4-(4-cyano-phenyl)-pyrrolidin-3-yl]-ethoxy}-nicotinonitrile (VI-B-5)

To a stirred solution of 4-[(3SR,4RS)-1-benzyl-4-((SR)-1-hydroxy-ethyl)-pyrrolidin-3-yl]-benzonitrile (V-A-5) (0.65 g, 2.12 mmol) in DMF (40 mL) at RT was added NaH (55% purity, 0.10 g, 4.1 mmol). After 10 minutes, 6-chloro-nicotinonitrile (0.32 g, 2.33 mmol) was added. The reaction mixture was stirred over night at RT, filtered on celite and concentrated under vacuo. Extraction with EtOAc/aq.NH₄Cl sat, followed by column chromatography (SiO₂, EtOAc/H, 1:1) yielded 0.39 g (45%) of the title compound as a colorless oil. ES-MS m/e: 409.3 (M+H⁺).

e) 6-{(SR)-1-[(3RS,4SR)-4-(4-Cyano-phenyl)-pyrrolidin-3-yl]-ethoxy}-nicotinonitrile (VII-B-5)

To a solution of 6-{(SR)-1-[(3RS,4SR)-1-benzyl-4-(4-cyano-phenyl)-pyrrolidin-3-yl]-ethoxy}-nicotinonitrile (VI-B-5) 380 mg (0.93 mmol) dissolved in toluene (10 mL) were added 0.30 mL (2.79 mmol) of 1-chloroethyl chloroformate and 0.47 mL (2.79 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 105 mg (35%) of the title compound as a light yellow oil. ES-MS m/e: 319.2 (M+H$^+$).

Pyrrolidine VII-B-6

4-{(3SR,4RS)-4-[1-((SR)-5-Trifluoromethyl-pyridin-2-yloxy)-ethyl]-pyrrolidin-3-yl}-benzonitrile

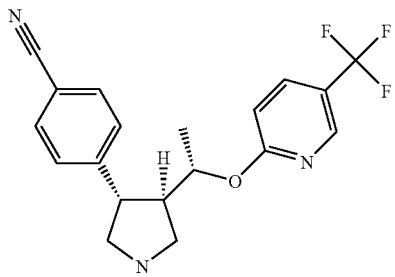

VII-B-6 a) 4-{(3 SR,4RS)-1-Benzyl-4-[1-((SR)-5-trifluoromethyl-pyridin-2-yloxy)-ethyl]-pyrrolidin-3-yl}-benzonitrile (VI-B-6)

To a stirred solution of 4-[(3SR,4RS)-1-benzyl-4-((SR)-1-hydroxy-ethyl)-pyrrolidin-3-yl]-benzonitrile (V-A-5) (0.65 g, 2.12 mmol, described herein above) in DMF (40 mL) at RT was added NaH (55% purity, 0.10 g, 4.1 mmol). After 10 minutes, 2-chloro-5-trifluoromethyl-pyridine (0.42 g, 2.33 mmol) was added. The reaction mixture was stirred over night at RT, filtered on celite and concentrated under vacuo. Extraction with EtOAc/aq.NH$_4$Cl sat, followed by column chromatography (SiO$_2$, EtOAc/H, 1:1) yielded 0.15 g (15%) of the title compound as a colorless oil. ES-MS m/e: 452.1 (M+H$^+$).

b) 4-{(3 SR,4RS)-4-[1-((SR)-5-Trifluoromethyl-pyridin-2-yloxy)-ethyl]-pyrrolidin-3-yl}-benzonitrile (VII-B-6)

To a solution of 4-{(3SR,4RS)-1-benzyl-4-[1-((SR)-5-trifluoromethyl-pyridin-2-yloxy)-ethyl]-pyrrolidin-3-yl}-benzonitrile (VI-B-6) 150 mg (0.33 mmol) dissolved in toluene (5 mL) were added 0.11 mL (1.00 mmol) of 1-chloroethyl chloroformate and 0.17 mL (1.00 mmol) of Hunig's base. The reaction mixture was heated at 100° C. for one hour. After cooling down to RT, volatiles were removed under vacuo and the crude was dissolved in MeOH (7.5 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 60 mg (50%) of the title compound as a colorless oil. ES-MS m/e: 362.2 (M+H$^+$).

Pyrrolidine VII-B-7

4-{(3SR,4RS)-4-[1-((SR)-5-Chloro-pyridin-2-yloxy)-ethyl]-pyrrolidin-3-yl}-benzonitrile

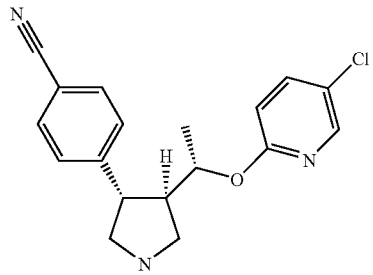

VII-B-7 a) 4-{(3 SR,4RS)-1-Benzyl-4-[1-((SR)-5-chloro-pyridin-2-yloxy)-ethyl]-pyrrolidin-3-yl}-benzonitrile (VI-B-7)

To a stirred solution of 4-[(3SR,4RS)-1-benzyl-4-((SR)-1-hydroxy-ethyl)-pyrrolidin-3-yl]-benzonitrile (V-A-5) (0.65 g, 2.12 mmol, described herein above) in DMF (40 mL) at RT was added NaH (55% purity, 0.10 g, 4.1 mmol). After 10 minutes, 2,5-dichloro-pyridine (0.34 g, 2.33 mmol) was added. The reaction mixture was stirred over night at RT, filtered on celite and concentrated under vacuo. Extraction with EtOAc/aq.NH$_4$Cl sat, followed by column chromatography (SiO$_2$, EtOAc/H, 1:1) yielded 0.75 g (78%) of the title compound as a colorless oil. ES-MS m/e: 418.3 (M+H$^+$).

b) 4-{(3 SR,4RS)-4-[1-((SR)-5-Chloro-pyridin-2-yloxy)-ethyl]-pyrrolidin-3-yl}-benzonitrile (VII-B-7)

To a solution of 4-{(3SR,4RS)-1-benzyl-4-[1-((SR)-5-chloro-pyridin-2-yloxy)-ethyl]-pyrrolidin-3-yl}-benzonitrile (VI-B-7) 700 mg (1.65 mmol) dissolved in toluene (20 mL) were added 0.54 mL (5.03 mmol) of 1-chloroethyl chloroformate and 0.85 mL (5.03 mmol) of Hunig's base. The reaction mixture was heated at 100° C. for one hour. After cooling down to RT, volatiles were removed under vacuo and the crude was dissolved in MeOH (30 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 260 mg (47%) of the title compound as a colorless oil. ES-MS m/e: 328.2 (M+H$^+$).

Pyrrolidine VII-B-8

5-Chloro-2-{(S)-1-[(3R,4S)-4-(4-chloro-phenyl)-pyrrolidin-3-yl]-ethoxy}-pyridine

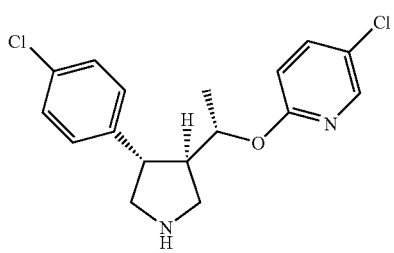

VII-B-8 a) 1-(1-Benzyl-2,5-dihydro-1H-pyrrol-3-yl)-ethanone

To a solution of N-(methoxymethyl)-N-(phenylmethyl)-N-(trimethylsilyl)methylamine (9.76 g, 0.041 mol) in $CH_2Cl_2$ (40 mL) at 0° C., was added dropwise over a 5 minutes period but-3-yn-2-one (2.0 g, 0.029 mol) followed by trifluoroacetic acid (0.22 mL, 0.003 mol) (very exothermic reaction). The ice bath was removed after 30 minutes, and the solution was stirred at 25° C. for an additional 2 h. It was then concentrated and purification by flash chromatography ($SiO_2$, EtOAc/Heptane 1:1) afforded 2.90 g (49%) of the title compound as a yellow oil. ES-MS m/e: 202.2 (M+H$^+$).

b) 1-[(3R,4S)-1-Benzyl-4-(4-chloro-phenyl)-pyrrolidin-3-yl]-ethanone (IV-8)

A two necked flask was charged under argon with rhodium (acac)bis ethylene (45 mg, 0.05 eq.), (R)-BINAP (110 mg, 0.05 eq.) and 4-chloro-phenylboronic acid (1.20 g, 2.2 eq.). 100 mL of MeOH and 10 mL of $H_2O$ were added followed by 1-(1-benzyl-2,5-dihydro-1H-pyrrol-3-yl)-ethanone (0.70 g). The reaction mixture was heated at 55° C. for 8 hours, cooled down to RT and concentrated under vacuo. Purification by flash chromatography ($SiO_2$, EtOAc/Heptane 2/1) afforded 0.36 g (33%) of the title product as a light yellow oil. ES-MS m/e: 314.0 (M+H$^+$).

c) (S)-1-[(3R,4S)-1-Benzyl-4-(4-chloro-phenyl)-pyrrolidin-3-yl]-ethanol (V-A-8) and (R)-1-[(3R,4S)-1-Benzyl-4-(4-chloro-phenyl)-pyrrolidin-3-yl]-ethanol (V-B-8)

To a solution of 1-[(3R,4S)-1-benzyl-4-(4-chloro-phenyl)-pyrrolidin-3-yl]-ethanone (0.52 g, 1.65 mmol) in THF (20 mL) at 0° C. were added portion wise $LiAlH_4$ (55 mg, 1.45 mmol). Stirring was continued for one hour, and the reaction mixture was carefully quenched by addition of aq. $NH_4Cl$, concentrated under vacuo and the product extracted with EtOAC. The combined organic phases were dried on $Na_2SO_4$ and concentrated under vacuo. The two diastereoisomeres were separated by column chromatography ($SiO_2$, EtOAc/H, 1:1) to yield (R)-1-[(3R,4S)-1-benzyl-4-(4-chloro-phenyl)-pyrrolidin-3-yl]-ethanol (V-B-8) 0.24 g (46%) as a white solid ES-MS m/e: 316.1 (M+H$^+$) and (S)-1-[(3R,4S)-1-benzyl-4-(4-chloro-phenyl)-pyrrolidin-3-yl]-ethanol (V-A-8) 0.25 g (47%) as a white solid ES-MS m/e: 316.1 (M+H$^+$).

d) 2-{(S)-1-[(3R,4S)-1-Benzyl-4-(4-chloro-phenyl)-pyrrolidin-3-yl]-ethoxy}-5-chloro-pyridine (VI-B-8)

To a suspension of $PPh_3$ ($PPh_3$ polymer bound, 3 mmol $PPh_3$/g resin) (0.44 g, 1.69 mmol) in THF (50 mL) at 0° C. were added 5-chloro-pyridin-2-ol (0.15 g, 1.15 mmol) and then DBAD (0.28 g, 1.23 mmol). After 5 minutes was added (R)-1-[(3R,4S)-1-benzyl-4-(4-chloro-phenyl)-pyrrolidin-3-yl]-ethanol (0.25 g, 0.79 mmol). The reaction mixture was stirred over night at RT, filtered on celite and concentrated under vacuo. Extraction with EtOAc/aq.NaOH 1M, followed by column chromatography ($SiO_2$, EtOAc/H, 1:3) yielded 0.22 g (65%) of the title compound as a colorless oil. ES-MS m/e: 427.8 (M+H$^+$).

e) 5-Chloro-2-{(S)-1-[(3R,4S)-4-(4-chloro-phenyl)-pyrrolidin-3-yl]-ethoxy}-pyridine (VII-B-8)

To a solution of 2-{(S)-1-[(3R,4S)-1-benzyl-4-(4-chloro-phenyl)-pyrrolidin-3-yl]-ethoxy}-5-chloro-pyridine 220 mg (0.51 mmol) dissolved in toluene (5 mL) were added 0.17 mL (1.53 mmol) of 1-chloroethyl chloroformate and 0.27 mL (1.53 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography ($SiO_2$, $CH_2Cl_2$/MeOH 9:1) yielded 110 mg (62%) of the title compound as a light yellow oil. ES-MS m/e: 337.1 (M+H$^+$).

Pyrrolidine VII-B-9

5-Chloro-2-{(S)-1-[(3R,4S)-4-(4-chloro-3-fluoro-phenyl)-pyrrolidin-3-yl]-ethoxy}-pyridine

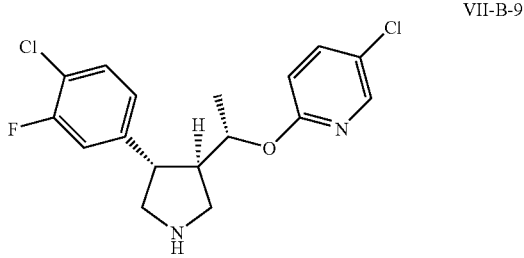

VII-B-9 a) 1-[(3R,4S)-1-Benzyl-4-(4-chloro-3-fluoro-phenyl)-pyrrolidin-3-yl]-ethanone (IV-9)

A two necked flask was charged under argon with rhodium (acac)bis ethylene (31 mg, 0.05 eq.), (R)-BINAP (74 mg, 0.05 eq.) and 4-chloro-3-fluoro-phenylboronic acid (825 mg, 2.5 eq.). 30 mL of MeOH and 3 mL of $H_2O$ were added followed by 1-(1-benzyl-2,5-dihydro-1H-pyrrol-3-yl)-ethanone (480 mg, described herein above). The reaction mixture was heated at 55° C. for 3 hours, cooled down to RT and concentrated under vacuo. Purification by flash chromatography (SiO₂, EtOAc/Heptane 2/1) afforded 261 mg (33%) of the title product as a light yellow oil. ES-MS m/e: 332.1 (M+H⁺).

b) (S)-1-[(3R,4S)-1-Benzyl-4-(4-chloro-3-fluoro-phenyl)-pyrrolidin-3-yl]-ethanol (IV-A-9) and (R)-1-[(3R,4S)-1-Benzyl-4-(4-chloro-3-fluoro-phenyl)-pyrrolidin-3-yl]-ethanol (IV-B-9)

To a solution of 1-[(3R,4S)-1-benzyl-4-(4-chloro-3-fluoro-phenyl)-pyrrolidin-3-yl]-ethanone (260 mg, 0.78 mmol) in THF (10 mL) at 0° C. were added portion wise LiAlH₄ (26 mg, 0.68 mmol). Stirring was continued for one hour, and the reaction mixture was carefully quenched by addition of aq. NH₄Cl, concentrated under vacuo and the product extracted with EtOAC. The combined organic phases were dried on Na₂SO₄ and concentrated under vacuo. The two diastereoisomeres were separated by column chromatography (SiO₂, EtOAc/H, 1:1) to yield (R)-1-[(3R,4S)-1-benzyl-4-(4-chloro-3-fluoro-phenyl)-pyrrolidin-3-yl]-ethanol (IV-B-9) 101 mg (38%) as a white solid ES-MS m/e: 334.2 (M+H⁺) and (S)-1-[(3R,4S)-1-benzyl-4-(4-chloro-3-fluoro-phenyl)-pyrrolidin-3-yl]-ethanol (IV-A-9) 80 mg (30%) as a white solid ES-MS m/e: 334.2 (M+H⁺).

c) 2-{(S)-1-[(3R,4S)-1-Benzyl-4-(4-chloro-3-fluoro-phenyl)-pyrrolidin-3-yl]-ethoxy}-5-chloro-pyridine (VI-B-9)

To a suspension of PPh₃ (PPh₃ polymer bound, 3 mmol PPh₃/g resin) (216 mg, 0.65 mmol) in THF (10 mL) at 0° C. were added 5-chloro-pyridin-2-ol (58 mg, 0.45 mmol) and then DBAD (110 mg, 0.48 mmol). After 5 minutes was added (R)-1-[(3R,4S)-1-benzyl-4-(4-chloro-3-fluoro-phenyl)-pyrrolidin-3-yl]-ethanol (100 mg, 0.30 mmol). The reaction mixture was stirred over night at RT, filtered on celite and concentrated under vacuo. Extraction with EtOAc/aq.NaOH 1M, followed by column chromatography (SiO₂, EtOAc/H, 1:3) yielded 100 mg (75%) of the title compound as a colorless oil. ES-MS m/e: 445.1 (M+H⁺).

d) 5-Chloro-2-{(S)-1-[(3R,4S)-1-(4-chloro-3-fluoro-phenyl)-pyrrolidin-3-yl]-ethoxy}-pyridine (VII-B-9)

To a solution of 2-{(S)-1-[(3R,4S)-1-benzyl-4-(4-chloro-3-fluoro-phenyl)-pyrrolidin-3-yl]-ethoxy}-5-chloro-pyridine 98 mg (0.22 mmol) dissolved in toluene (5 mL) were added 0.072 mL (0.66 mmol) of 1-chloroethyl chloroformate and 0.11 mL (0.66 mL) of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 75 mg (95%) of the title compound as a light yellow oil. ES-MS m/e: 355.1 (M+H⁺).

Pyrrolidine Intermediates of Formula VIII-B

Pyrrolidine VIII-B-1

6-{(SR)-1-[(3RS,4SR)-4-(3,4-Dichloro-phenyl)-1-(piperidine-4-carbonyl)-pyrrolidin-3-yl]-ethoxy}-nicotinonitrile

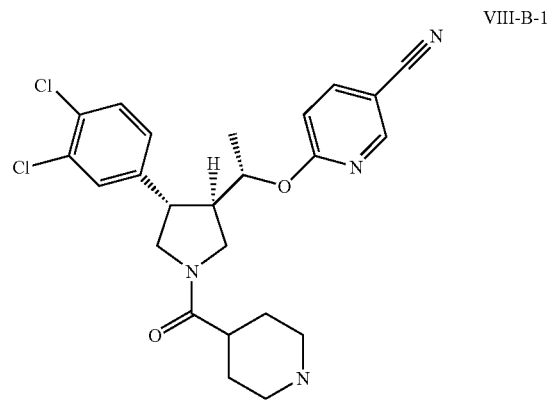

VIII-B-1 a) 4-[(3RS,4SR)-3-[(SR)-1-(5-Cyano-pyridin-2-yloxy)-ethyl]-4-(3,4-dichloro-phenyl)-pyrrolidine-1-carbonyl]-piperidine-1-carboxylic acid tert-butyl ester To a stirred solution of piperidine-1,4-dicarboxylic acid mono-tert-butyl ester (0.165 g, 0.72 mmol) in 20 mL of CH₂Cl₂ was added (0.14 g, 0.94 mmol) of EDC, (0.10 g, 0.94 mmol) of HOBt and Et₃N (0.11 mL, 1.1 mmol). After one hour at RT, was added 6-{(SR)-1-[(3RS,4SR)-4-(3,4-dichloro-phenyl)-pyrrolidin-3-yl]-ethoxy}-nicotinonitrile (VII-B-2, 0.26 g, 0.72 mmol). The mixture was stirred at RT over night and then poured onto water and extracted with CH₂Cl₂. The combined organic phases were dried over Na₂SO₄ and concentrated under vacuo. Column chromatography (SiO₂, EtOAc/H, 1:1) yielded 0.29 g (91%) of the title compound as a white foam. ES-MS m/e: 574.8 (M+H⁺).

b) 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)

To a stirred solution of 4-[(3RS,4SR)-3-[(SR)-1-(5-cyano-pyridin-2-yloxy)-ethyl]-4-(3,4-dichloro-phenyl)-pyrrolidine-1-carbonyl]-piperidine-1-carboxylic acid tert-butyl ester (0.28 g, 0.50 mmol) in 24 mL of CH₂Cl₂ was added 6 mL of TFA. After one hour at RT, the reaction was quenched by addition of aq. NaOH 1M (until ph=10) and the product was extracted with CH₂Cl₂. The combined organic phases were dried over Na₂SO₄ and concentrated under vacuo to yield 0.237 g (99%) of the title compound as a white foam. ES-MS m/e: 473.0 (M+H⁺). Pyrrolidine VIII-B-2

6-{(SR)-1-[(3RS,4SR)-1-(Azetidine-3-carbonyl)-4-(3,4-dichloro-phenyl)-pyrrolidin-3-yl]-ethoxy}-nicotinonitrile

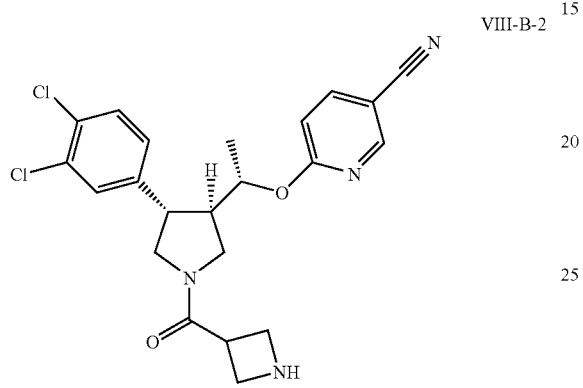

VIII-B-2 a) 3-[(3R,4S)-3-[(S)-1-(5-Cyano-pyridin-2-yloxy)-ethyl]-4-(3,4-dichloro-phenyl)-pyrrolidine-1-carbonyl]-azetidine-1-carboxylic acid tert-butyl ester To a stirred solution of azetidine-1,3-dicarboxylic acid mono-tert-butyl ester (0.072 g, 0.36 mmol) in 15 mL of CH₂Cl₂ was added (0.069 g, 0.36 mmol) of EDC, (0.048 g, 0.36 mmol) of HOBt and Et₃N (0.06 mL, 0.42 mmol). After one hour at RT, was added 6-{(SR)-1-[(3RS,4SR)-4-(3,4-dichloro-phenyl)-pyrrolidin-3-yl]-ethoxy}-nicotinonitrile (VII-B-2, 0.10 g, 0.27 mmol). The mixture was stirred at RT over night and then poured onto water and extracted with CH₂Cl₂. The combined organic phases were dried over Na₂SO₄ and concentrated under vacuo. Column chromatography (SiO₂, EtOAc/H, 1:1) yielded 0.14 g (98%) of the title compound as a white solid. ES-MS m/e: 545.3 (M+H⁺).

b) 6-{(SR)-1-[(3RS,4SR)-1-(Azetidine-3-carbonyl)-4-(3,4-dichloro-phenyl)-pyrrolidin-3-yl]-ethoxy}-nicotinonitrile (VIII-B-2)

To a stirred solution of 3-[(3R,4S)-3-[(S)-1-(5-cyano-pyridin-2-yloxy)-ethyl]-4-(3,4-dichloro-phenyl)-pyrrolidine-1-carbonyl]-azetidine-1-carboxylic acid tert-butyl ester (0.14 g, 0.25 mmol) in 4 mL of CH₂Cl₂ was added 1 mL of TFA. After one hour at RT, the reaction was quenched by addition of aq. NaOH 1M (until ph=10) and the product was extracted with CH₂Cl₂. The combined organic phases were dried over Na₂SO₄ and concentrated under vacuo to yield 0.106 g (92%) of the title compound as a white foam. ES-MS m/e: 445.1 (M+H⁺).

Example 1

1-{4-[(3RS,4SR)-3-[(SR)-1-(5-Chloro-pyridin-2-yloxy)-ethyl]-4-(3,4-dichloro-phenyl)-pyrrolidine-1-carbonyl]-piperidin-1-yl}-ethanone

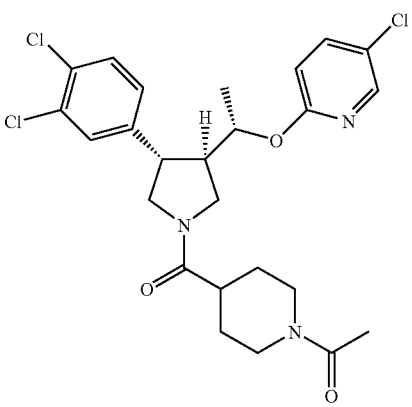

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)
Carboxylic acid: 1-Acetyl-piperidine-4-carboxylic acid (commercially available), ES-MS m/e: 524.3 (M+H⁺).

Example 2

6-{(SR)-1-[(3RS,4SR)-1-(1-Acetyl-piperidine-4-carbonyl)-4-(3,4-dichloro-phenyl)-pyrrolidin-3-yl]-ethoxy}-nicotinonitrile

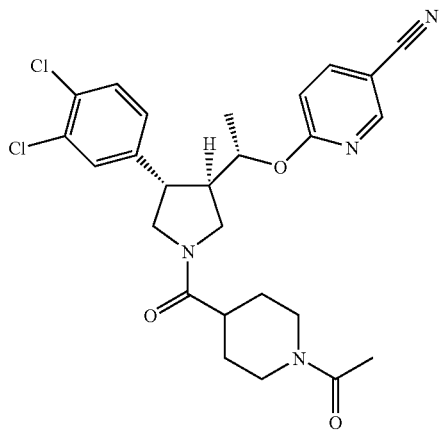

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: 1-Acetyl-piperidine-4-carboxylic acid (commercially available),
ES-MS m/e: 515.0 (M+H⁺).

Example 3

[(3RS,4SR)-3-[(SR)-1-(5-Chloro-pyridin-2-yloxy)-ethyl]-4-(3,4-dichloro-phenyl)-pyrrolidin-1-yl]-(1-cyclobutanecarbonyl-piperidin-4-yl)-methanone

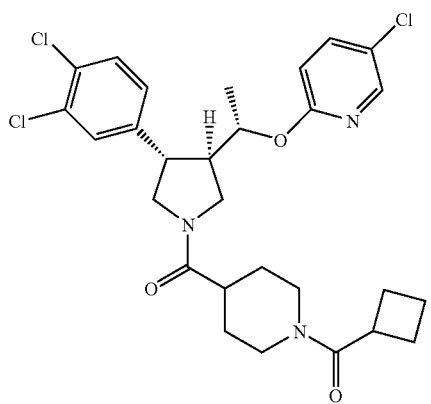

Coupling according to general procedure I:

Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)

Carboxylic acid: 1-Cyclobutanecarbonyl-piperidine-4-carboxylic acid (commercially available), ES-MS m/e: 565.7 (M+H$^+$).

Example 4

[(3RS,4SR)-3-[(SR)-1-(5-Chloro-pyridin-2-yloxy)-ethyl]-4-(3,4-dichloro-phenyl)-pyrrolidin-1-yl]-(1-methyl-piperidin-4-yl)-methanone

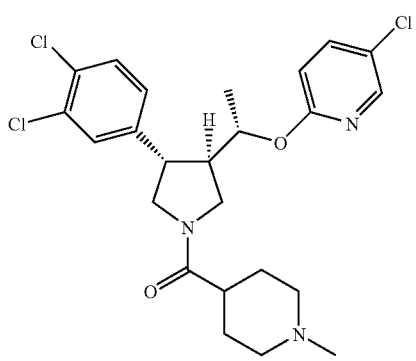

Coupling according to general procedure I:

Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)

Carboxylic acid: 1-Methyl-piperidine-4-carboxylic acid (commercially available), ES-MS m/e: 496.04 (M+H$^+$).

Example 5

{4-[(3RS,4SR)-3-[(SR)-1-(5-Chloro-pyridin-2-yloxy)-ethyl]-4-(3,4-dichloro-phenyl)-pyrrolidine-1-carbonyl]-cyclohexyl}-carbamic acid methyl ester

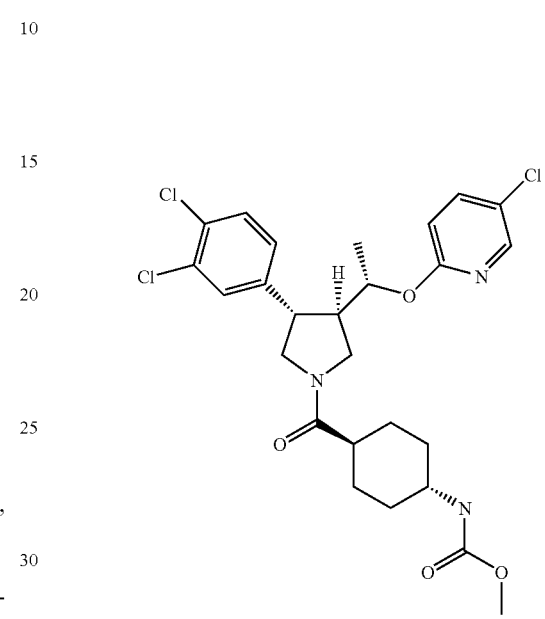

Coupling according to general procedure I:

Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)

Carboxylic acid: 4-Methoxycarbonylamino-cyclohexanecarboxylic acid,

ES-MS m/e: 555.72 (M+H$^+$).

4-Methoxycarbonylamino-cyclohexanecarboxylic acid

To a stirred solution of trans-4-amino-cyclohexanecarboxylic acid methyl ester (commercially available) in CH$_2$Cl$_2$ was added Et$_3$N (2 eq.) and methyl-chloroformate (1.05 eq.). Stirring was continued overnight at RT. The reaction was quenched by addition of H$_2$O, the product was extracted with CH$_2$Cl$_2$ and the organic phase washed with aq. HCl 1M. The combined organic phases were dried over Na$_2$SO$_4$ and concentrated under vacuo. The residue was dissolved in MeOH and a 2M KOH aq. solution was added. The reaction was stirred at RT 4 hours, aq. HCl was added until ph=6, and then the product was extracted with EtOAc. The combined organic phases were dried over Na$_2$SO$_4$ and concentrated under vacuo to afford the title product as a white foam which was used in the next step without further purification.

Example 6

[(3RS,4SR)-3-[(SR)-1-(5-Chloro-pyridin-2-yloxy)-ethyl]-4-(3,4-dichloro-phenyl)-pyrrolidin-1-yl]-(4-methoxymethyl-cyclohexyl)-methanone

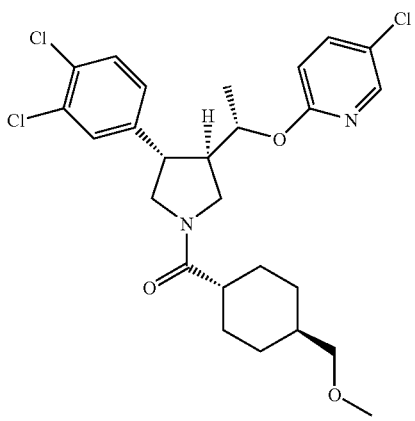

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)
Carboxylic acid: 4-Methoxymethyl-cyclohexanecarboxylic acid (described in JP60258141),
ES-MS m/e: 526.8 (M+H⁺).

Example 7

6-{(SR)-1-[(3RS,4SR)-4-(3,4-Dichloro-phenyl)-1-(piperidine-4-carbonyl)-pyrrolidin-3-yl]-ethoxy}-nicotinonitrile

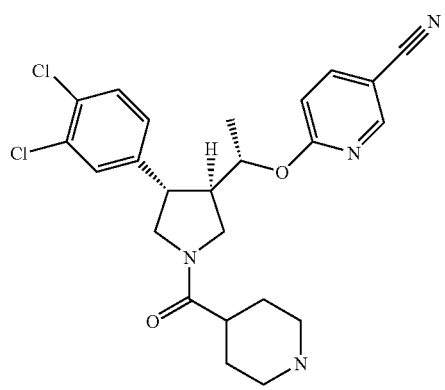

a) 4-[(3RS 4SR)-3-[(SR)-1-(5-Cyano-pyridin-2-yloxy)-ethyl]-4-(3,4-dichloro-phenyl)-pyrrolidine-1-carbonyl]-piperidine-1-carboxylic acid tert-butyl ester To a stirred solution of piperidine-1,4-dicarboxylic acid mono-tert-butyl ester (0.165 g, 0.72 mmol) in 20 mL of CH₂Cl₂ was added (0.14 g, 0.94 mmol) of EDC, (0.10 g, 0.94 mmol) of HOBt and Et₃N (0.11 mL, 1.1 mmol). After one hour at RT, was added 6-{(SR)-1-[(3RS,4SR)-4-(3,4-dichloro-phenyl)-pyrrolidin-3-yl]-ethoxy}-nicotinonitrile (VII-B-2, 0.26 g, 0.72 mmol). The mixture was stirred at RT over night and then poured onto water and extracted with CH₂Cl₂. The combined organic phases were dried over Na₂SO₄ and concentrated under vacuo. Column chromatography (SiO₂, EtOAc/H, 1:1) yielded 0.29 g (91%) of the title compound as a white foam.

b) 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)

To a stirred solution of 4-[(3RS,4SR)-3-[(SR)-1-(5-cyano-pyridin-2-yloxy)-ethyl]-4-(3,4-dichloro-phenyl)-pyrrolidine-1-carbonyl]-piperidine-1-carboxylic acid tert-butyl ester (0.28 g, 0.50 mmol) in 24 mL of CH₂Cl₂ was added 6 mL of TFA. After one hour at RT, the reaction was quenched by addition of aq. NaOH 1M (until ph=10) and the product was extracted with CH₂Cl₂. The combined organic phases were dried over Na₂SO₄ and concentrated under vacuo to yield 0.237 g (99%) of the title compound as a white foam. ES-MS m/e: 473.0 (M+H⁺).

Example 8

[(3RS,4SR)-3-[(SR)-1-(5-Chloro-pyridin-2-yloxy)-ethyl]-4-(3,4-dichloro-phenyl)-pyrrolidin-1-yl]-((2R,4S,5S)-3,4-dihydroxy-cyclohexyl)-methanone

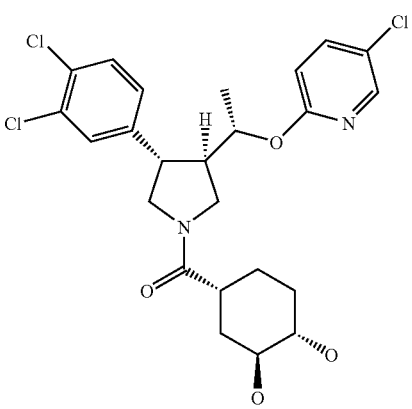

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)

Carboxylic acid: (1R,3S,4S)-3,4-Dihydroxy-cyclohexanecarboxylic acid (commercially available), ES-MS m/e: 513.3 (M+H$^+$).

Example 9

[(3RS,4SR)-3-[(SR)-1-(5-Chloro-pyridin-2-yloxy)-ethyl]-4-(3,4-dichloro-phenyl)-pyrrolidin-1-yl]-((2S,4S,5S)-3,4-dihydroxy-cyclohexyl)-methanone

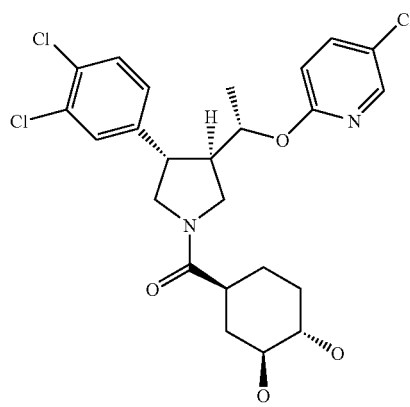

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)
Carboxylic acid: (1S,3S,4S)-3,4-Dihydroxy-cyclohexanecarboxylic acid (described in patent WO2006/016167), ES-MS m/e: 513.3 (M+H$^+$).

Example 10

[(3RS,4SR)-3-[(SR)-1-(5-Chloro-pyridin-2-yloxy)-ethyl]-4-(3,4-dichloro-phenyl)-pyrrolidin-1-yl]-(4-ethynyl-cyclohexyl)-methanone

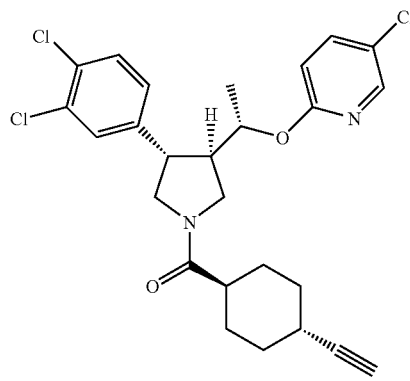

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)
Carboxylic acid: 4-Ethynyl-cyclohexanecarboxylic acid (commercially available),
ES-MS m/e: 506.9 (M+H$^+$).

Example 11

[(3RS,4SR)-3-[(SR)-1-(5-Chloro-pyridin-2-yloxy)-ethyl]-4-(3,4-dichloro-phenyl)-pyrrolidin-1-yl]-(1-isobutyl-piperidin-4-yl)-methanone

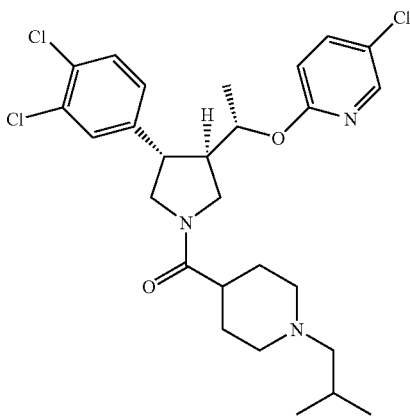

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)
Carboxylic acid: 1-Isobutyl-piperidine-4-carboxylic acid (commercially available),
ES-MS m/e: 540.3 (M+H$^+$).

Example 12

4-[(3RS,4SR)-3-[(SR)-1-(5-Chloro-pyridin-2-yloxy)-ethyl]-4-(3,4-dichloro-phenyl)-pyrrolidine-1-carbonyl]-cyclohexanone

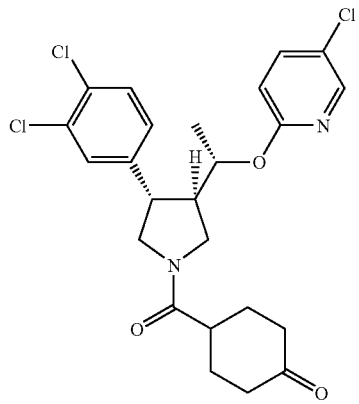

Coupling according to general procedure I:
Pyrrolidine intermediate: 5-Chloro-2-{(SR)-1-[(3RS,4SR)-4-(3,4-dichloro-phenyl)-pyrrolidin-3-yl]-ethoxy}-pyridine (VII-B-1)
Carboxylic acid: 4-Oxo-cyclohexanecarboxylic acid (commercially available),
ES-MS m/e: 497.0 (M+H$^+$).

Example 13

4-[(3RS,4SR)-3-[(SR)-1-(5-Cyano-pyridin-2-yloxy)-ethyl]-4-(3,4-dichloro-phenyl)-pyrrolidine-1-carbonyl]-piperidine-1-carboxylic acid tert-butyl ester

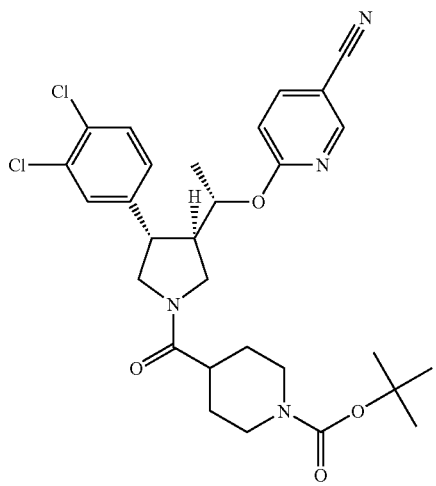

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: Piperidine-1,4-dicarboxylic acid mono-tert-butyl ester (commercially available), ES-MS m/e: 572.7 (M+H⁺).

Example 14

6-{(SR)-1-[(3RS,4SR)-1-(1-Cyclopropanecarbonyl-piperidine-4-carbonyl)-4-(3,4-dichloro-phenyl)-pyrrolidin-3-yl]-ethoxy}-nicotinonitrile

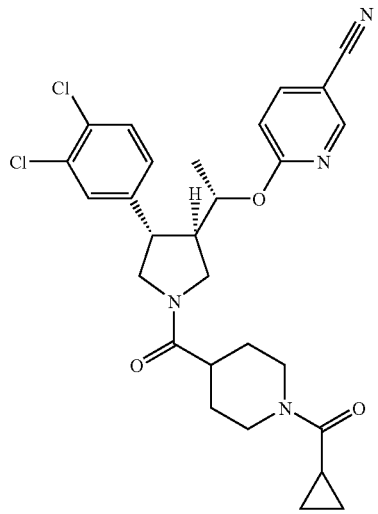

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)

Carboxylic acid: Cyclopropanecarboxylic acid (commercially available), ES-MS m/e: 540.9 (M+H⁺).

Example 15

{(3SR,4RS)-3-(3,4-Dichloro-phenyl)-4-[(SR)-1-(5-trifluoromethyl-pyridin-2-yloxy)-ethyl]-pyrrolidin-1-yl}-(tetrahydro-pyran-4-yl)-methanone

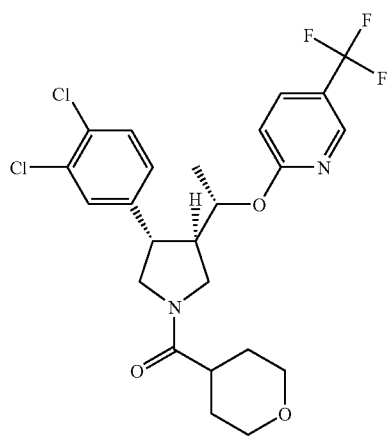

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (VII-B-3)
Carboxylic acid: Tetrahydro-pyran-4-carboxylic acid (commercially available), ES-MS m/e: 517.3 (M+H⁺).

Example 16

6-{(SR)-1-[(3RS,4SR)-1-[1-(1-Cyano-cyclopropanecarbonyl)-piperidine-4-carbonyl]-4-(3,4-dichloro-phenyl)-pyrrolidin-3-yl]-ethoxy}-nicotinonitrile

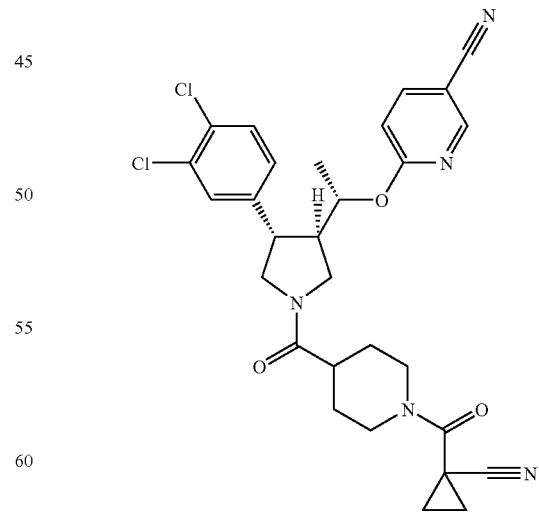

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)

Carboxylic acid: 1-Cyano-cyclopropanecarboxylic acid (commercially available), ES-MS m/e: 566.4 (M+H⁺).

Example 17

6-((SR)-1-{(3RS,4SR)-4-(3,4-Dichloro-phenyl)-1-[1-(1-methyl-cyclopropanecarbonyl)-piperidine-4-carbonyl]-pyrrolidin-3-yl}-ethoxy)-nicotinonitrile

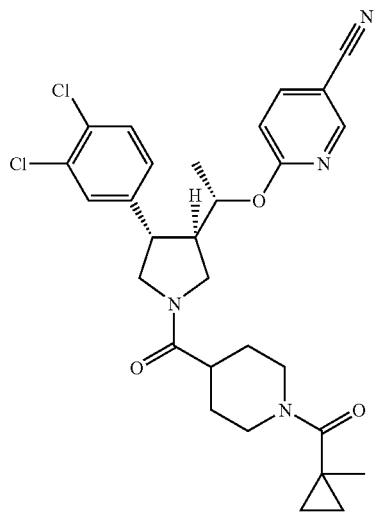

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Carboxylic acid: 1-Methyl-cyclopropanecarboxylic acid (commercially available),
ES-MS m/e: 555.2 (M+H⁺).

Example 18

6-((SR)-1-{(3RS,4SR)-4-(3,4-Dichloro-phenyl)-1-[1-(2,2-difluoro-cyclopropanecarbonyl)-piperidine-4-carbonyl]-pyrrolidin-3-yl}-ethoxy)-nicotinonitrile

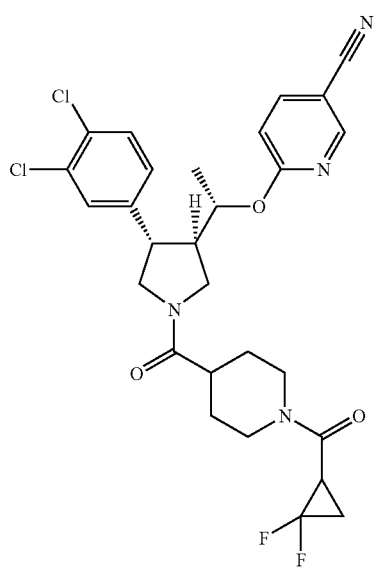

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Carboxylic acid: 2,2-Difluoro-cyclopropanecarboxylic acid (commercially available),
ES-MS m/e: 577.3 (M+H⁺).

Example 19

6-{(SR)-1-[(3RS,4SR)-1-[1-(1-Amino-cyclopropanecarbonyl)-piperidine-4-carbonyl]-4-(3,4-dichloro-phenyl)-pyrrolidin-3-yl]-ethoxy}-nicotinonitrile

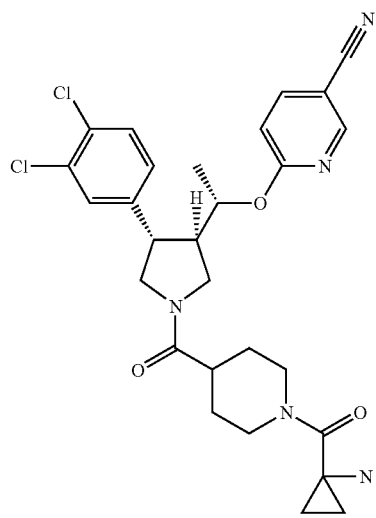

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Carboxylic acid: 1-Amino-cyclopropanecarboxylic acid (commercially available),
ES-MS m/e: 556.2 (M+H⁺).

Example 20

6-{(SR)-1-[(3RS,4SR)-1-(1-Cyclobutanecarbonyl-piperidine-4-carbonyl)-4-(3,4-dichloro-phenyl)-pyrrolidin-3-yl]-ethoxy}-nicotinonitrile

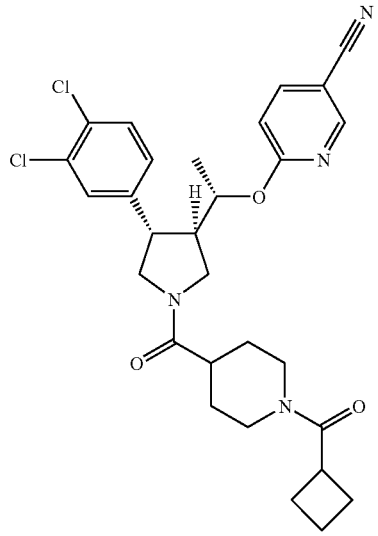

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Carboxylic acid: Cyclobutanecarboxylic acid (commercially available),
ES-MS m/e: 555.2 (M+H$^+$).

Example 21

6-((SR)-1-{(3RS,4SR)-4-(3,4-Dichloro-phenyl)-1-[1-(3-oxo-cyclobutanecarbonyl)-piperidine-4-carbonyl]-pyrrolidin-3-yl}-ethoxy)-nicotinonitrile

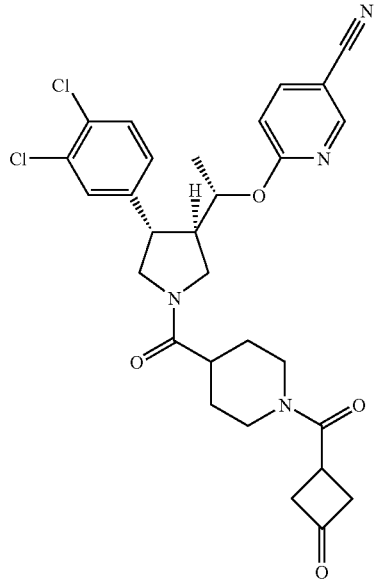

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Carboxylic acid: 3-Oxo-cyclobutanecarboxylic acid (commercially available),
ES-MS m/e: 569.3 (M+H$^+$).

Example 22

6-{(SR)-1-[(3RS,4SR)-4-(3,4-Dichloro-phenyl)-1-(1-propionyl-piperidine-4-carbonyl)-pyrrolidin-3-yl]-ethoxy}-nicotinonitrile

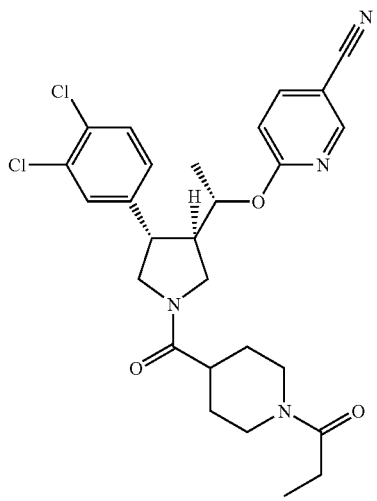

Coupling according to general procedure II:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Acid chlorid: Propionyl chloride (commercially available),
ES-MS m/e: 529.2 (M+H$^+$).

Example 23

6-{(SR)-1-[(3RS,4SR)-1-[1-(2-Cyano-acetyl)-piperidine-4-carbonyl]-4-(3,4-dichloro-phenyl)-pyrrolidin-3-yl]-ethoxy}-nicotinonitrile

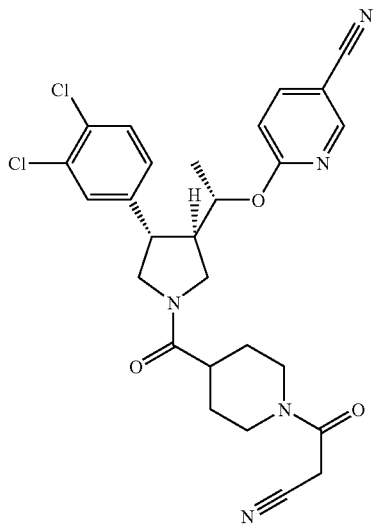

Coupling according to general procedure I:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Carboxylic acid: Cyano-acetic acid (commercially available),
ES-MS m/e: 540.3 (M+H$^+$).

Example 24

6-((SR)-1-{(3RS,4SR)-4-(3,4-Dichloro-phenyl)-1-[1-(2-methoxy-acetyl)-piperidine-4-carbonyl]-pyrrolidin-3-yl}-ethoxy)-nicotinonitrile

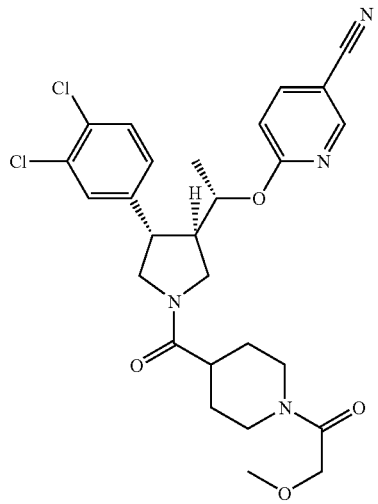

Coupling according to general procedure II:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Acid chlorid: Methoxy-acetyl chloride (commercially available),
ES-MS m/e: 545.2 (M+H$^+$).

Example 25

6-{(SR)-1-[(3RS,4SR)-1-(1-Acetyl-azetidine-3-carbonyl)-4-(3,4-dichloro-phenyl)-pyrrolidin-3-yl]-ethoxy}-nicotinonitrile

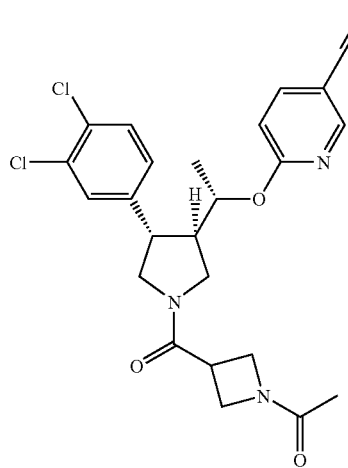

Coupling according to general procedure II:
Pyrrolidine intermediate: 6-{(SR)-1-[(3RS,4SR)-1-(Azetidine-3-carbonyl)-4-(3,4-dichloro-phenyl)-pyrrolidin-3-yl]-ethoxy}-nicotinonitrile (VIII-B-2)
Acid chlorid: Acetyl chloride (commercially available),
ES-MS m/e: 487.3 (M+H$^+$).

Example 26

6-{(SR)-1-[(3RS,4SR)-1-(1-Cyclopropanecarbonyl-azetidine-3-carbonyl)-4-(3,4-dichloro-phenyl)-pyrrolidin-3-yl]-ethoxy}-nicotinonitrile

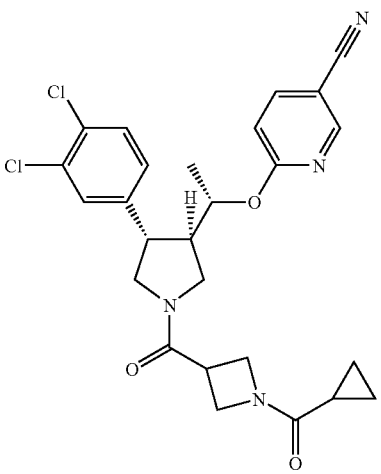

Coupling according to general procedure I:
Pyrrolidine intermediate: 6-{(SR)-1-[(3RS,4SR)-1-(Azetidine-3-carbonyl)-4-(3,4-dichloro-phenyl)-pyrrolidin-3-yl]-ethoxy}-nicotinonitrile (VIII-B-2)
Carboxylic acid: Cyclopropanecarboxylic acid (commercially available),
ES-MS m/e: 513.4 (M+H$^+$).

Example 27

6-{(SR)-1-[(3RS,4SR)-1-[1-(1-Cyano-cyclopropanecarbonyl)-azetidine-3-carbonyl]-4-(3,4-dichloro-phenyl)-pyrrolidin-3-yl]-ethoxy}-nicotinonitrile

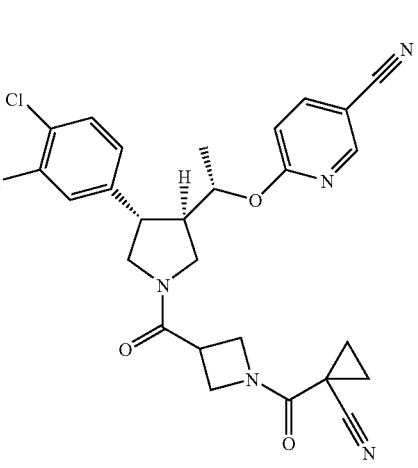

Coupling according to general procedure I:
Pyrrolidine intermediate: 6-{(SR)-1-[(3RS,4SR)-1-(Azetidine-3-carbonyl)-4-(3,4-dichloro-phenyl)-pyrrolidin-3-yl]-ethoxy}-nicotinonitrile (VIII-B-2)
Carboxylic acid: 1-Cyano-cyclopropanecarboxylic acid (commercially available),
ES-MS m/e: 538.3 (M+H⁺).

Example 28

6-{(SR)-1-[(3RS,4SR)-1-[1-(2-Cyano-acetyl)-azetidine-3-carbonyl]-4-(3,4-dichloro-phenyl)-pyrrolidin-3-yl]-ethoxy}-nicotinonitrile

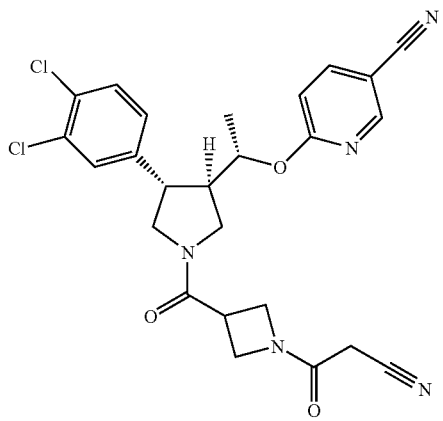

Coupling according to general procedure I:
Pyrrolidine intermediate: 6-{(SR)-1-[(3RS,4SR)-1-(Azetidine-3-carbonyl)-4-(3,4-dichloro-phenyl)-pyrrolidin-3-yl]-ethoxy}-nicotinonitrile (VIII-B-2)
Carboxylic acid: Cyano-acetic acid (commercially available),
ES-MS m/e: 512.4 (M+H⁺).

Example 29

3-[(3RS,4SR)-3-[(SR)-1-(5-Cyano-pyridin-2-yloxy)-ethyl]-4-(3,4-dichloro-phenyl)-pyrrolidine-1-carbonyl]-azetidine-1-carboxylic acid tert-butyl ester

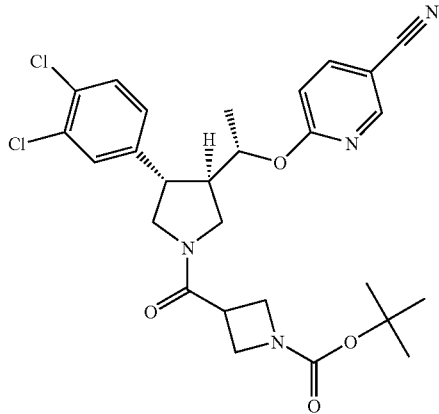

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: Azetidine-1,3-dicarboxylic acid mono-tert-butyl ester (commercially available), ES-MS m/e: 545.3 (M+H⁺).

Example 30

6-{(SR)-1-[(3RS,4SR)-1-(Azetidine-3-carbonyl)-4-(3,4-dichloro-phenyl)-pyrrolidin-3-yl]-ethoxy}-nicotinonitrile

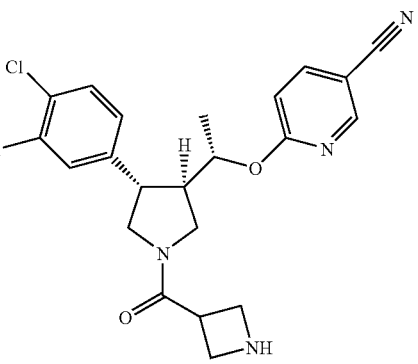

a) 3-[(3R,4S)-3-[(S)-1-(5-Cyano-pyridin-2-yloxy)-ethyl]-4-(3,4-dichloro-phenyl)-pyrrolidine-1-carbonyl]-azetidine-1-carboxylic acid tert-butyl ester To a stirred solution of azetidine-1,3-dicarboxylic acid mono-tert-butyl ester (0.072 g, 0.36 mmol) in 15 mL of CH₂Cl₂ was added (0.069 g, 0.36 mmol) of EDC, (0.048 g, 0.36 mmol) of HOBt and Et₃N (0.06 mL, 0.42 mmol). After one hour at RT, was added 6-{(SR)-1-[(3RS,4SR)-4-(3,4-dichloro-phenyl)-pyrrolidin-3-yl]-ethoxy}-nicotinonitrile (VII-B-2, 0.10 g, 0.27 mmol). The mixture was stirred at RT over night and then poured onto water and extracted with CH₂Cl₂. The combined organic phases were dried over Na₂SO₄ and concentrated under vacuo. Column chromatography (SiO₂, EtOAc/H, 1:1) yielded 0.14 g (98%) of the title compound as a white solid.

b) 6-{(SR)-1-[(3RS,4SR)-1-(Azetidine-3-carbonyl)-4-(3,4-dichloro-phenyl)-pyrrolidin-3-yl]-ethoxy}-nicotinonitrile (VIII-B-2)

To a stirred solution of 3-[(3R,4S)-3-[(S)-1-(5-cyano-pyridin-2-yloxy)-ethyl]-4-(3,4-dichloro-phenyl)-pyrrolidine-1-carbonyl]-azetidine-1-carboxylic acid tert-butyl ester (0.14 g, 0.25 mmol) in 4 mL of CH₂Cl₂ was added 1 mL of TFA. After one hour at RT, the reaction was quenched by addition of aq. NaOH 1M (until ph=10) and the product was extracted with CH₂Cl₂. The combined organic phases were dried over Na₂SO₄ and concentrated under vacuo to yield 0.106 g (92%) of the title compound as a white foam. ES-MS m/e: 445.1 (M+H⁺).

Example 31

{(3SR,4RS)-3-(3,4-Dichloro-phenyl)-4-[(SR)-1-(5-trifluoromethyl-pyridin-2-yloxy)-ethyl]-pyrrolidin-1-yl}-(1-methyl-piperidin-4-yl)-methanone

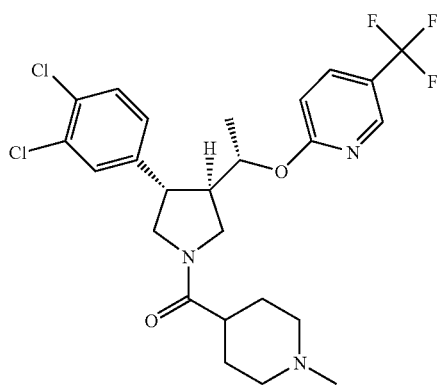

Coupling according to general procedure I:

Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (VII-B-3)

Carboxylic acid: 1-Methyl-piperidine-4-carboxylic acid (commercially available), ES-MS m/e: 529.9 (M+H⁺).

Example 32

3-[(3RS,4SR)-3-[(SR)-1-((S)-5-Cyano-pyridin-2-yloxy)-ethyl]-4-(3,4-dichloro-phenyl)-pyrrolidine-1-carbonyl]-pyrrolidine-1-carboxylic acid tert-butyl ester

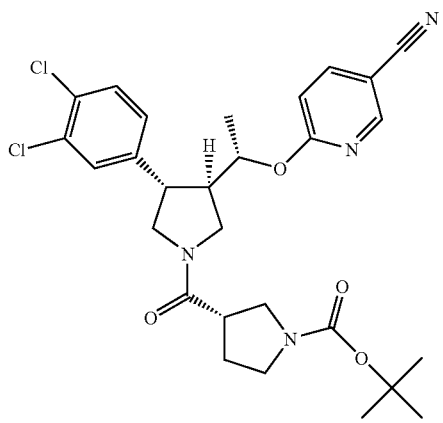

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)

Carboxylic acid: (S)-Pyrrolidine-1,3-dicarboxylic acid 1-tert-butyl ester (commercially available), ES-MS m/e: 558.7 (M+H⁺).

Example 33

3-[(3RS,4SR)-3-[(SR)-1-((R)-5-Cyano-pyridin-2-yloxy)-ethyl]-4-(3,4-dichloro-phenyl)-pyrrolidine-1-carbonyl]-pyrrolidine-1-carboxylic acid tert-butyl ester

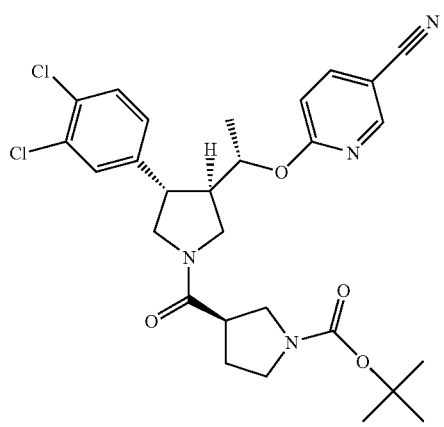

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)

Carboxylic acid: (R)-Pyrrolidine-1,3-dicarboxylic acid 1-tert-butyl ester (commercially available), ES-MS m/e: 558.7 (M+H⁺).

Example 34

6-{(SR)-1-[(3RS,4SR)-1-(1-Cyanomethyl-piperidine-4-carbonyl)-4-(3,4-dichloro-phenyl)-pyrrolidin-3-yl]-ethoxy}-nicotinonitrile

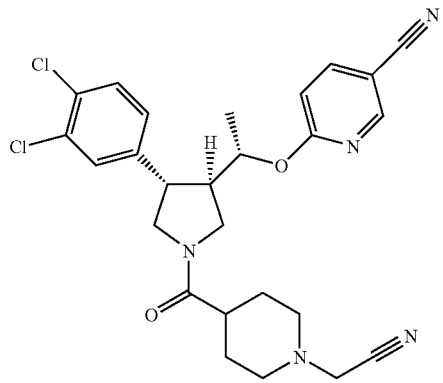

To a stirred solution of 6-{(SR)-1-[(3RS,4SR)-4-(3,4-dichloro-phenyl)-1-(piperidine-4-carbonyl)-pyrrolidin-3-yl]-ethoxy}-nicotinonitrile (VIII-B-1) (25 mg, 0.053 mmol) in THF (2 mL) was added NaH (2.4 mg, 55% purity, 0.056 mmol). After 10 min. 2-iodo acetonitrile (13 mg, 0.079 mmol) was added and stirring was continued at RT overnight.

The reaction was quenched with H₂O, and the product extracted with EtOAc. The combined organic phases were dried over Na₂SO₄, concentrated under vacuo and the residue was purified by column chromatography (SiO₂, CH₂Cl₂/MeOH 9/1) to yield 20 mg (74%) of the title compound as a light brown foam. ES-MS m/e: 512.0 (M+H⁺).

Example 35

4-[(3RS,4SR)-3-[(SR)-1-(5-Cyano-pyridin-2-yloxy)-ethyl]-4-(3,4-dichloro-phenyl)-pyrrolidine-1-carbonyl]-piperidine-1-carboxylic acid methyl ester

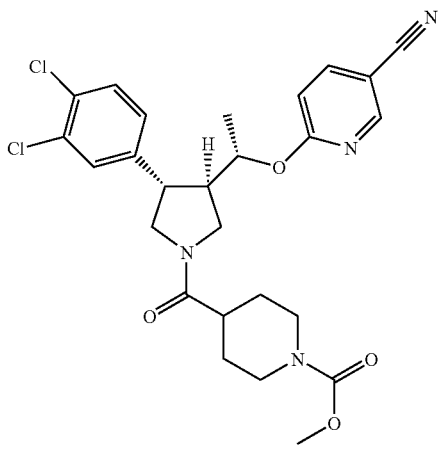

Coupling according to general procedure II:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Chloroformate: Methyl chloroformate (commercially available), ES-MS m/e: 531.6 (M+H⁺).

Example 36

6-{(SR)-1-[(3RS,4SR)-4-(3,4-Dichloro-phenyl)-1-(pyrrolidine-3-carbonyl)-pyrrolidin-3-yl]-ethoxy}-nicotinonitrile

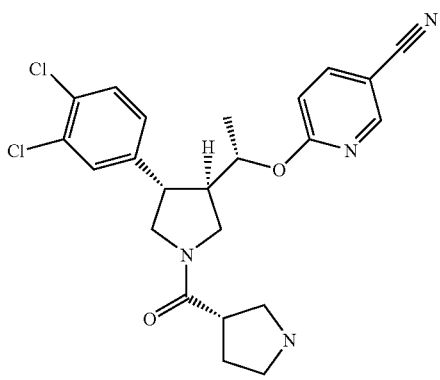

To a stirred solution of 3-[(3RS,4SR)-3-[(SR)-1-((S)-5-cyano-pyridin-2-yloxy)-ethyl]-4-(3,4-dichloro-phenyl)-pyrrolidine-1-carbonyl]-pyrrolidine-1-carboxylic acid tert-butyl ester (described herein above) (80 mg, 0.140 mmol) in CH₂Cl₂ (4 mL) was added TFA (1 mL). Stirring was continued at RT for 1 hour, and an aqueous solution of NaHCO₃ was added (until ph=8). The product was extracted with CH₂Cl₂ and the combined organic phase dried over Na₂SO₄. Concentration under vacuo afforded 64 mg (97%) of the title compound as a white solid. ES-MS m/e: 459.1 (M+H⁺).

Example 37

6-{(SR)-1-[(3RS,4SR)-4-(3,4-Dichloro-phenyl)-1-(pyrrolidine-3-carbonyl)-pyrrolidin-3-yl]-ethoxy}-nicotinonitrile

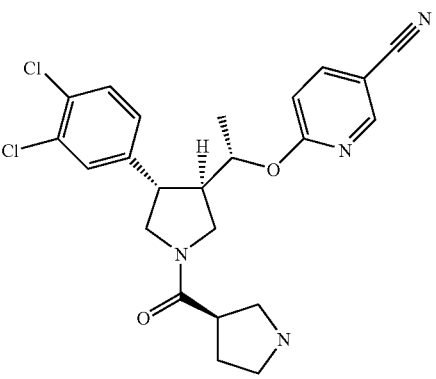

To a stirred solution of 3-[(3RS,4SR)-3-[(SR)-1-((R)-5-Cyano-pyridin-2-yloxy)-ethyl]-4-(3,4-dichloro-phenyl)-pyrrolidine-1-carbonyl]-pyrrolidine-1-carboxylic acid tert-butyl ester (described herein above) (80 mg, 0.140 mmol) in CH₂Cl₂ (4 mL) was added TFA (1 mL). Stirring was continued at RT for 1 hour, and an aqueous solution of NaHCO₃ was added (until ph=8). The product was extracted with CH₂Cl₂ and the combined organic phase dried over Na₂SO₄. Concentration under vacuo afforded 62 mg (94%) of the title compound as a white solid. ES-MS m/e: 459.1 (M+H⁺).

Example 38

6-{(SR)-1-[(3RS,4SR)-1-(1-Acetyl-pyrrolidine-3-carbonyl)-4-(3,4-dichloro-phenyl)-pyrrolidin-3-yl]-ethoxy}-nicotinonitrile

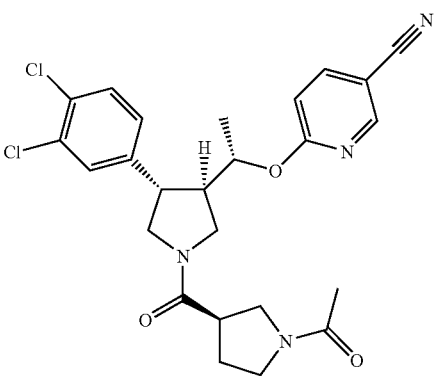

Coupling according to general procedure II:
Intermediate: 6-{(SR)-1-[(3RS,4SR)-4-(3,4-dichloro-phenyl)-1-(pyrrolidine-3-carbonyl)-pyrrolidin-3-yl]-ethoxy}-nicotinonitrile (described hereinabove)

Acid chlorid: Acetyl chloride (commercially available),
ES-MS m/e: 500.9 (M+H⁺).

Example 39

6-{(SR)-1-[(3RS,4SR)-4-(3,4-Dichloro-phenyl)-1-(1-methanesulfonyl-piperidine-4-carbonyl)-pyrrolidin-3-yl]-ethoxy}-nicotinonitrile

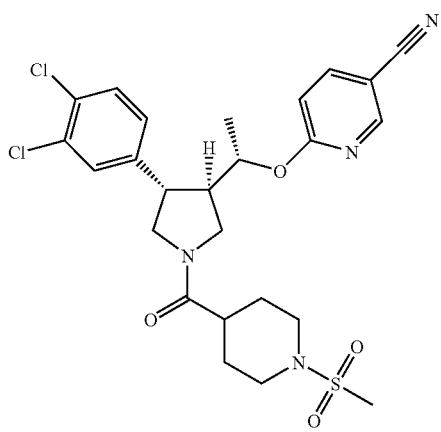

Coupling according to general procedure II:
Pyrrolidine intermediate: 6-{(SR)-1-[(3RS,4SR)-4-(3,4-Dichloro-phenyl)-1-(piperidine-4-carbonyl)-pyrrolidin-3-yl]-ethoxy}-nicotinonitrile (VIII-B-1)
Sulfonyl chlorid: Methanesulfonyl chloride (commercially available),
ES-MS m/e: 551.6 (M+H⁺).

Example 40

6-{(SR)-1-[(3RS,4SR)-1-(1-Acetyl-piperidine-3-carbonyl)-4-(3,4-dichloro-phenyl)-pyrrolidin-3-yl]-ethoxy}-nicotinonitrile

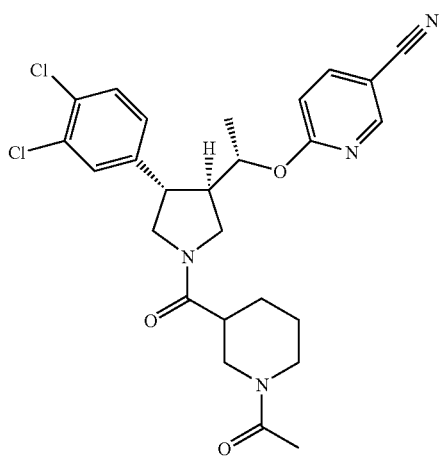

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: 1-Acetyl-piperidine-3-carboxylic acid (commercially available),
ES-MS m/e: 515.2 (M+H⁺).

Example 41

3-[(3RS,4SR)-3-[(SR)-1-(5-Cyano-pyridin-2-yloxy)-ethyl]-4-(3,4-dichloro-phenyl)-pyrrolidine-1-carbonyl]-piperidine-1-carboxylic acid tert-butyl ester

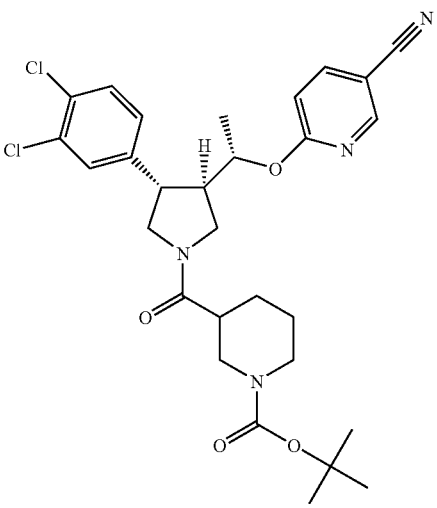

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: Piperidine-1,3-dicarboxylic acid 1-tert-butyl ester (commercially available),
ES-MS m/e: 573.2 (M+H⁺).

Example 42

{4-[(3RS,4SR)-3-[(SR)-1-(5-Cyano-pyridin-2-yloxy)-ethyl]-4-(3,4-dichloro-phenyl)-pyrrolidine-1-carbonyl]-cyclohexyl}-methyl-carbamic acid tert-butyl ester

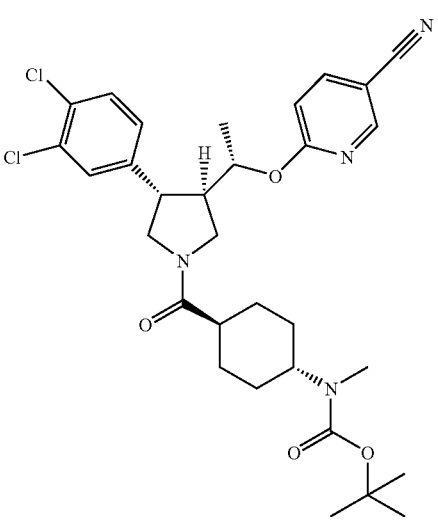

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)

Carboxylic acid: trans-4-(tert-Butoxycarbonyl-methyl-amino)-cyclohexanecarboxylic acid (described in US20050065210), ES-MS m/e: 601.3 (M+H⁺).

Example 43

{4-[(3RS,4SR)-3-[(SR)-1-(5-Cyano-pyridin-2-yloxy)-ethyl]-4-(3,4-dichloro-phenyl)-pyrrolidine-1-carbonyl]-cyclohexyl}-carbamic acid tert-butyl ester

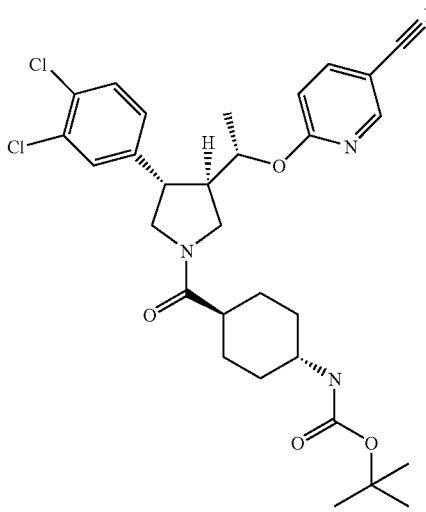

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: trans-4-tert-Butoxycarbonylamino-cyclohexanecarboxylic acid (commercially available), ES-MS m/e: 587.2 (M+H⁺).

Example 44

6-{(SR)-1-[(3RS,4SR)-4-(3,4-Dichloro-phenyl)-1-(4-methylamino-cyclohexanecarbonyl)-pyrrolidin-3-yl]-ethoxy}-nicotinonitrile

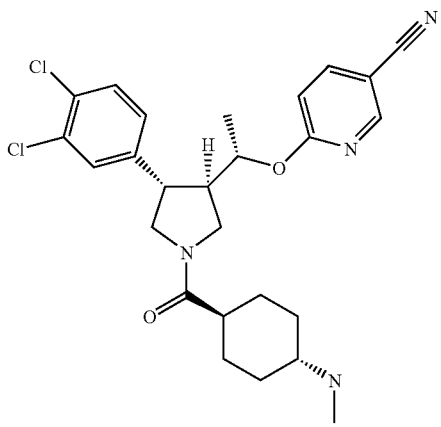

To a stirred solution of {4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-methyl-carbamic acid tert-butyl ester described herein above (30 mg, 0.050 mmol) in $CH_2Cl_2$ (4 mL) was added TFA (1 mL). After 1 hour, aqueous NaHCO₃ was added until ph=8, the product was extracted with $CH_2Cl_2$. The combined organic phases were dried over $Na_2SO_4$ to give the title product as a colorless oil (25 mg, 98%). ES-MS m/e: 500.9 (M+H⁺).

Example 45

N-{4-[(3RS,4SR)-3-[(SR)-1-(5-Cyano-pyridin-2-yloxy)-ethyl]-4-(3,4-dichloro-phenyl)-pyrrolidine-1-carbonyl]-cyclohexyl}-N-methyl-acetamide

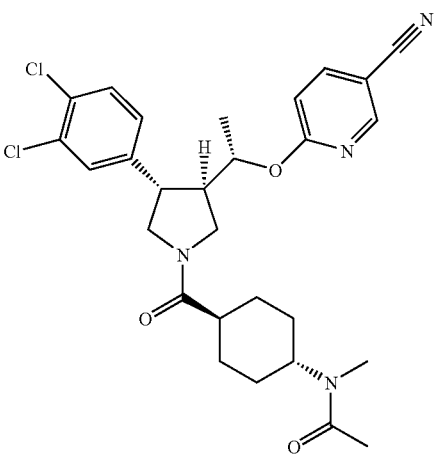

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)
Carboxylic acid: 4-(Acetyl-methyl-amino)-cyclohexane carboxylic acid (described in JP2006298909), ES-MS m/e: 542.9 (M+H⁺).

Example 46

1-(4-{(3SR,4RS)-3-(3,4-Dichloro-phenyl)-4-[(SR)-1-(5-trifluoromethyl-pyridin-2-yloxy)-ethyl]-pyrrolidine-1-carbonyl}-piperidin-1-yl)-ethanone

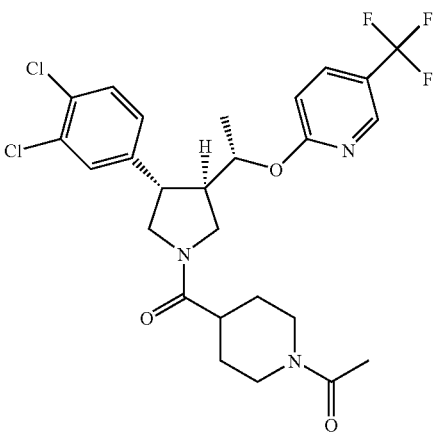

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (VII-B-3)
Carboxylic acid: 1-Acetyl-piperidine-4-carboxylic acid (commercially available),
ES-MS m/e: 558.1 (M+H⁺).

Example 47

6-((SR)-1-{(3RS,4SR)-4-(3,4-Dichloro-phenyl)-1-[1-(1-methyl-cyclopropanecarbonyl)-piperidine-4-carbonyl]-pyrrolidin-3-yl}-ethoxy)-nicotinonitrile

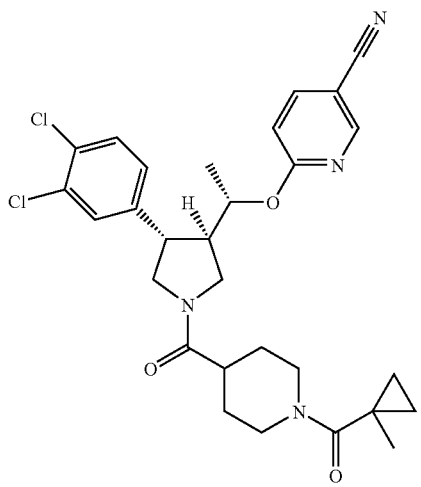

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (VII-B-2)

Carboxylic acid: 1-(1-Methyl-cyclopropanecarbonyl)-piperidine-4-carboxylic acid (described herein after), ES-MS m/e: 592.0 (M+H$^+$).

1-(1-Methyl-cyclopropanecarbonyl)-piperidine-4-carboxylic acid a) 1-(1-Methyl-cyclopropanecarbonyl)-piperidine-4-carboxylic acid ethyl ester To a stirred solution of 1-methyl-cyclopropanecarboxylic acid (14.4 g, 0.144 mol) in 200 mL of CH$_2$Cl$_2$ was added (27.10 g, 0.141 mol) of EDC, (19.10 g, 0.141 g) of HOBt and Et$_3$N (35.93 mL, 0.259 mol). After one hour at RT, was added piperidine-4-carboxylic acid ethyl ester (18.90 g, 0.120 mol). The mixture was stirred at RT over night and then poured onto water and extracted with CH$_2$Cl$_2$. The combined organic phases were dried over Na$_2$SO$_4$ and concentrated under vacuo. Column chromatography (SiO$_2$, EtOAc/H, 1:1) yielded 26.1 g (92%) of the title compound as a light yellow oil.

b) 1-(1-Methyl-cyclopropanecarbonyl)-piperidine-4-carboxylic acid

To a stirred solution of 1-(1-Methyl-cyclopropanecarbonyl)-piperidine-4-carboxylic acid ethyl ester (26.09 g, 0.109 mol) in 500 mL of a mixture of THF, EtOH and H$_2$O (1/1/1) was added LiOH.H$_2$O (6.86 g, 0.163 mol). After one hour at RT, the solvent were evaporated and the residue taken up in CH$_2$Cl$_2$ and the organic phase was washed with aqueous HCl 1M. The organic phases were dried over Na$_2$SO$_4$ and evaporated under vacuo to gave 19.8 g (86%) of the title compound as a white solid. ES-MS m/e: 212.1 (M+H$^+$).

Example 48

[(3RS,4SR)-3-[(SR)-1-(5-Chloro-pyridin-2-yloxy)-ethyl]-4-(2,4-difluoro-phenyl)-pyrrolidin-1-yl]-[1-(1-methyl-cyclopropanecarbonyl)-piperidin-4-yl]-methanone

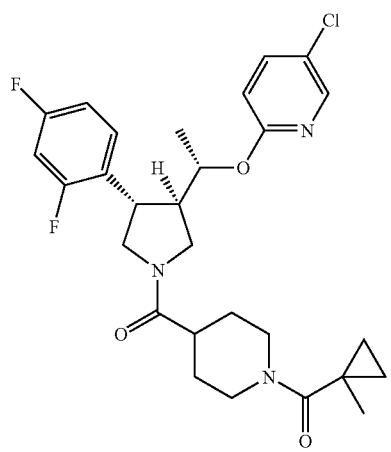

Coupling according to general procedure I:

Pyrrolidine intermediate: 5-Chloro-2-{(SR)-1-[(3RS,4SR)-4-(2,4-difluoro-phenyl)-pyrrolidin-3-yl]-ethoxy}-pyridine (VII-B-4)

Carboxylic acid: 1-(1-Methyl-cyclopropanecarbonyl)-piperidine-4-carboxylic acid (described herein after), ES-MS m/e: 532.2 (M+H$^+$).

1-(1-Methyl-cyclopropanecarbonyl)-piperidine-4-carboxylic acid a) 1-(1-Methyl-cyclopropanecarbonyl)-piperidine-4-carboxylic acid ethyl ester To a stirred solution of 1-methyl-cyclopropanecarboxylic acid (14.4 g, 0.144 mol) in 200 mL of CH$_2$Cl$_2$ was added (27.10 g, 0.141 mol) of EDC, (19.10 g, 0.141 g) of HOBt and Et$_3$N (35.93 mL, 0.259 mol). After one hour at RT, was added piperidine-4-carboxylic acid ethyl ester (18.90 g, 0.120 mol). The mixture was stirred at RT over night and then poured onto water and extracted with CH$_2$Cl$_2$. The combined organic phases were dried over Na$_2$SO$_4$ and concentrated under vacuo. Column chromatography (SiO$_2$, EtOAc/H, 1:1) yielded 26.1 g (92%) of the title compound as a light yellow oil.

b) 1-(1-Methyl-cyclopropanecarbonyl)-piperidine-4-carboxylic acid

To a stirred solution of 1-(1-Methyl-cyclopropanecarbonyl)-piperidine-4-carboxylic acid ethyl ester (26.09 g, 0.109 mol) in 500 mL of a mixture of THF, EtOH and H$_2$O (1/1/1) was added LiOH.H$_2$O (6.86 g, 0.163 mol). After one hour at RT, the solvent were evaporated and the residue taken up in CH$_2$Cl$_2$ and the organic phase was washed with aqueous HCl 1M. The organic phases were dried over Na$_2$SO$_4$ and evapo-

Example 49

6-{(SR)-1-[(3RS,4SR)-1-(1-Acetyl-piperidine-4-carbonyl)-4-(4-cyano-phenyl)-pyrrolidin-3-yl]-ethoxy}-nicotinonitrile

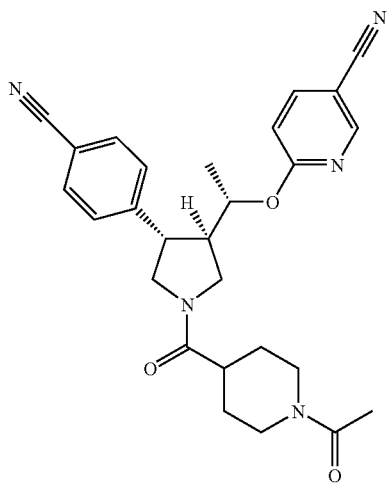

Coupling according to general procedure I:
Pyrrolidine intermediate: 6-{(SR)-1-[(3RS,4SR)-4-(4-Cyano-phenyl)-pyrrolidin-3-yl]-ethoxy}-nicotinonitrile (VII-B-5)
Carboxylic acid: 1-Acetyl-piperidine-4-carboxylic acid (commercially available),
ES-MS m/e: 472.3 (M+H$^+$).

Example 50

4-{(3SR,4RS)-1-(1-Acetyl-piperidine-4-carbonyl)-4-[(SR)-1-(5-trifluoromethyl-pyridin-2-yloxy)-ethyl]-pyrrolidin-3-yl}-benzonitrile

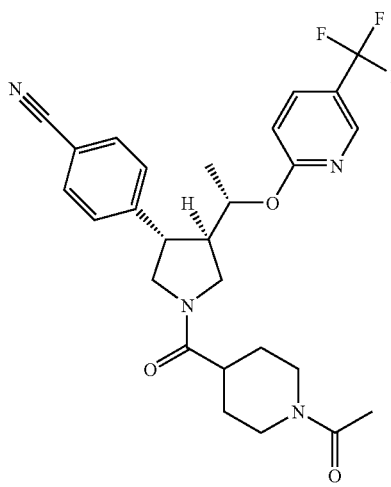

Coupling according to general procedure I:
Pyrrolidine intermediate: 4-{(3SR,4RS)-4-[1-((SR)-5-Trifluoromethyl-pyridin-2-yloxy)-ethyl]-pyrrolidin-3-yl}-benzonitrile (VII-B-6)
Carboxylic acid: 1-Acetyl-piperidine-4-carboxylic acid (commercially available),
ES-MS m/e: 515.3 (M+H$^+$).

Example 51

4-{(3SR,4RS)-1-(1-Acetyl-piperidine-4-carbonyl)-4-[(SR)-1-(5-chloro-pyridin-2-yloxy)-ethyl]-pyrrolidin-3-yl}-benzonitrile

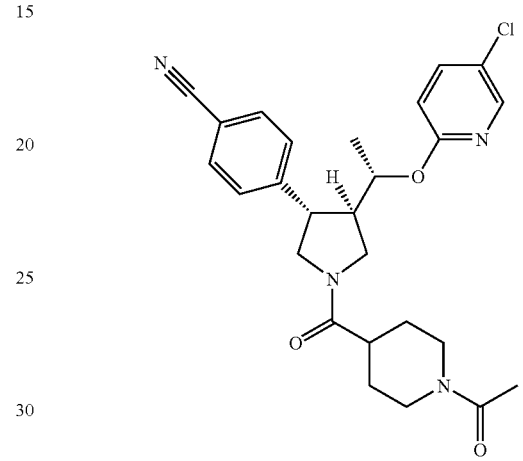

Coupling according to general procedure I:
Pyrrolidine intermediate: 4-{(3SR,4RS)-4-[1-((SR)-5-Chloro-pyridin-2-yloxy)-ethyl]-pyrrolidin-3-yl}-benzonitrile (VII-B-7)
Carboxylic acid: 1-Acetyl-piperidine-4-carboxylic acid (commercially available),
ES-MS m/e: 481.2 (M+H$^+$).

Example 52

{(3S,4R)-3-(4-Chloro-phenyl)-4-[(S)-1-(5-chloro-pyridin-2-yloxy)-ethyl]-pyrrolidin-1-yl}-[1-(1-methyl-cyclopropanecarbonyl)-piperidin-4-yl]-methanone

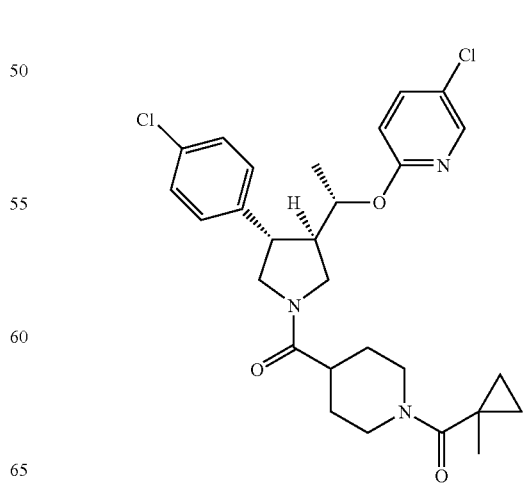

Coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-8)
Carboxylic acid: 1-(1-Methyl-cyclopropanecarbonyl)-piperidine-4-carboxylic acid (described herein after),
ES-MS m/e: 530.1 (M+H⁺).

1-(1-Methyl-cyclopropanecarbonyl)-piperidine-4-carboxylic acid a) 1-(1-Methyl-cyclopropanecarbonyl)-piperidine-4-carboxylic acid ethyl ester To a stirred solution of 1-methyl-cyclopropanecarboxylic acid (14.4 g, 0.144 mol) in 200 mL of CH$_2$Cl$_2$ was added (27.10 g, 0.141 mol) of EDC, (19.10 g, 0.141 g) of HOBt and Et$_3$N (35.93 mL, 0.259 mol). After one hour at RT, was added piperidine-4-carboxylic acid ethyl ester (18.90 g, 0.120 mol). The mixture was stirred at RT overnight and then poured onto water and extracted with CH$_2$Cl$_2$. The combined organic phases were dried over Na$_2$SO$_4$ and concentrated under vacuo. Column chromatography (SiO$_2$, EtOAc/H, 1:1) yielded 26.1 g (92%) of the title compound as a light yellow oil.

b) 1-(1-Methyl-cyclopropanecarbonyl)-piperidine-4-carboxylic acid

To a stirred solution of 1-(1-Methyl-cyclopropanecarbonyl)-piperidine-4-carboxylic acid ethyl ester (26.09 g, 0.109 mol) in 500 mL of a mixture of THF, EtOH and H$_2$O) (1/1/1) was added LiOH.H$_2$O) (6.86 g, 0.163 mol). After one hour at RT, the solvent were evaporated and the residue taken up in CH$_2$Cl$_2$ and the organic phase was washed with aqueous HCl 1M. The organic phases were dried over Na$_2$SO$_4$ and evaporated under vacuo to gave 19.8 g (86%) of the title compound as a white solid. ES-MS m/e: 212.1 (M+H⁺).

Example 53

{(3S,4R)-3-(4-Chloro-3-fluoro-phenyl)-4-[(S)-1-(5-chloro-pyridin-2-yloxy)-ethyl]-pyrrolidin-1-yl}-[1-(1-methyl-cyclopropanecarbonyl)-piperidin-4-yl]-methanone

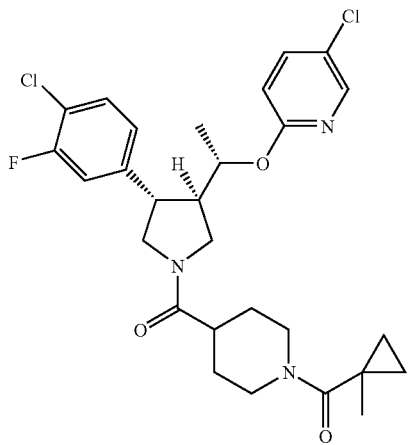

Coupling according to general procedure I:
Pyrrolidine intermediate: 5-Chloro-2-{(S)-1-[(3R,4S)-4-(4-chloro-3-fluoro-phenyl)-pyrrolidin-3-yl]-ethoxy}-pyridine (VII-B-9)
Carboxylic acid: 1-(1-Methyl-cyclopropanecarbonyl)-piperidine-4-carboxylic acid (described herein after), ES-MS m/e: 548.2 (M+H⁺).

1-(1-Methyl-cyclopropanecarbonyl)-piperidine-4-carboxylic acid a) 1-(1-Methyl-cyclopropanecarbonyl)-piperidine-4-carboxylic acid ethyl ester To a stirred solution of 1-methyl-cyclopropanecarboxylic acid (14.4 g, 0.144 mol) in 200 mL of CH$_2$Cl$_2$ was added (27.10 g, 0.141 mol) of EDC, (19.10 g, 0.141 g) of HOBt and Et$_3$N (35.93 mL, 0.259 mol). After one hour at RT, was added piperidine-4-carboxylic acid ethyl ester (18.90 g, 0.120 mol). The mixture was stirred at RT overnight and then poured onto water and extracted with CH$_2$Cl$_2$. The combined organic phases were dried over Na$_2$SO$_4$ and concentrated under vacuo. Column chromatography (SiO$_2$, EtOAc/H, 1:1) yielded 26.1 g (92%) of the title compound as a light yellow oil.

b) 1-(1-Methyl-cyclopropanecarbonyl)-piperidine-4-carboxylic acid

To a stirred solution of 1-(1-Methyl-cyclopropanecarbonyl)-piperidine-4-carboxylic acid ethyl ester (26.09 g, 0.109 mol) in 500 mL of a mixture of THF, EtOH and H$_2$O) (1/1/1) was added LiOH.H$_2$O) (6.86 g, 0.163 mol). After one hour at RT, the solvent were evaporated and the residue taken up in CH$_2$Cl$_2$ and the organic phase was washed with aqueous HCl 1M. The organic phases were dried over Na$_2$SO$_4$ and evaporated under vacuo to gave 19.8 g (86%) of the title compound as a white solid. ES-MS m/e: 212.1 (M+H⁺).

The invention claimed is:
1. A compound of formula I

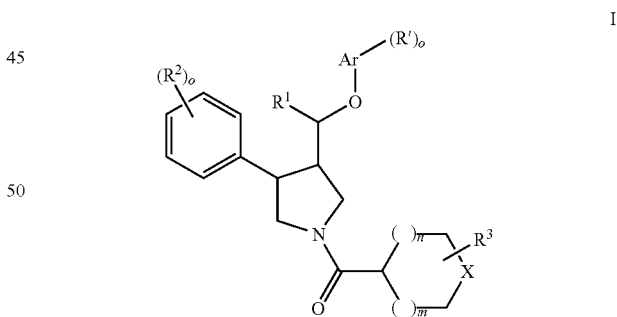

wherein
R$^1$ is hydrogen or lower alkyl;
each R$^2$ is independently halogen, CN, lower alkyl, or lower alkyl substituted by halogen;
Ar is aryl or heteroaryl;
R' is hydrogen, lower alkyl, halogen, cyano or lower alkyl substituted by halogen;
R$^3$ is hydrogen, lower alkyl or hydroxy;
X is —CH(R$^4$)—, —N(R$^{4'}$)— or —O—;
R$^4$ is hydrogen, hydroxy, =O, lower alkyl, lower alkynyl, —S(O)$_2$-lower alkyl, —C(O)-lower alkyl, —C(O)

CH₂O-lower alkyl, —CH₂CN, —C(O)CH₂CN, —C(O)-cycloalkyl wherein the cycloalkyl group is optionally substituted by cyano, lower alkyl, one or two halogen atoms, =O or amino, or is
—C(O)O-lower alkyl, —NH-lower alkyl, —NRC(O)O-lower alkyl, —NRC(O)-lower alkyl or —CH₂O-lower alkyl;

R⁴' is hydrogen, lower alkyl, —S(O)₂-lower alkyl, —C(O)-lower alkyl, —C(O)CH₂—O-lower alkyl, —CH₂CN, —C(O)CN, —C(O)CH₂CN, —C(O)-cycloalkyl wherein the cycloalkyl group is optionally substituted by cyano, lower alkyl, one or two halogen atoms, =O or amino, or is —C(O)O-lower alkyl or —CH₂O-lower alkyl;

R is hydrogen or lower alkyl; or

R³ and R⁴ together with the carbon atoms to which they are attached form a five or six-membered non aromatic ring or R³ and R⁴' together with the nitrogen and carbon atoms to which they are attached form a five or six-membered non aromatic ring;

n is 0 or 1;
m is 0, 1, or 2 when n is 0; or
m is 0 or 1 when n is 1; and
o is 0, 1, 2 or 3;

or a pharmaceutically active salt, racemic mixture, enantiomer, optical isomer or tautomeric form thereof.

2. A compound of claim 1,

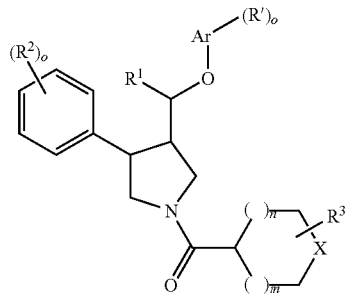

wherein
R¹ is lower alkyl;
each R² is independently halogen or CN;
Ar is heteroaryl;
R' is halogen, cyano or lower alkyl substituted by halogen;
R³ is hydrogen or hydroxy;
X is —CH(R⁴)—, —N(R⁴')— or —O—;
R⁴ is hydrogen, hydroxy, =O, lower alkynyl, —S(O)₂-lower alkyl, —NH-lower alkyl, —NRC(O)O-lower alkyl, —NRC(O)-lower alkyl or —CH₂O-lower alkyl;
R⁴' is hydrogen, lower alkyl, —S(O)₂-lower alkyl, —C(O)-lower alkyl, —C(O)CH₂—O-lower alkyl, —CH₂CN, —C(O)CH₂CN, —C(O)-cycloalkyl wherein the cycloalkyl group is optionally substituted by cyano, lower alkyl, one or two halogen atoms, =O or amino, or is —C(O)O-lower alkyl;
R is hydrogen or lower alkyl;
n is 0 or 1;
m is 0, 1, or 2 when n is 0; or
m is 0 or 1 when n is 1; and
o is 1 or 2;
or a pharmaceutically active salt, racemic mixture, enantiomer, optical isomer or tautomeric form thereof.

3. A compound of claim 2, wherein Ar is pyridinyl.
4. A compound of claim 3, wherein X is —CH(R⁴)—.
5. A compound of claim 4, selected from the group consisting of
{4-[(3RS,4SR)-3-[(SR)-1-(5-chloro-pyridin-2-yloxy)-ethyl]-4-(3,4-dichloro-phenyl)-pyrrolidine-1-carbonyl]-cycloheyl}-carbamic acid methyl ester;
[(3RS,4SR)-3-[(SR)-1-(5-chloro-pyridin-2-yloxy)-ethyl]-4-(3,4-dichloro-phenyl)-pyrrolidin-1-yl]-(4-methoxymethyl-cyclohexyl)-methanone;
[(3RS,4SR)-3-[(SR)-1-(5-chloro-pyridin-2-yloxy)-ethyl]-4-(3,4-dichloro-phenyl)-pyrrolidin-1-yl]-(4-ethynyl-cyclohexyl)-methanone;
4-[(3RS,4SR)-3-[(SR)-1-(5-chloro-pyridin-2-yloxy)-ethyl]-4-(3,4-dichloro-phenyl)-pyrrolidine-1-carbonyl]-cyclohexanone;
{4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-methyl-carbamic acid tert-butyl ester;
{4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-carbamic acid tert-butyl ester; and
N-{4-[(3RS,4SR)-3-[(SR)-1-(5-cyano-pyridin-2-yloxy)-ethyl]-4-(3,4-dichloro-phenyl)-pyrrolidine-1-carbonyl]-cyclohexyl}-N-methyl-acetamide.

6. A compound of claim 3, wherein X is —N(R⁴')—.
7. A compound of claim 6, wherein the compounds are
1-{4-[(3RS,4SR)-3-[(SR)-1-(5-chloro-pyridin-2-yloxy)-ethyl]-4-(3,4-dichloro-phenyl)-pyrrolidine-1-carbonyl]-piperidin-1-yl}-ethanone;
6-{(SR)-1-[(3RS,4SR)-1-(1-acetyl-piperidine-4-carbonyl)-4-(3,4-dichloro-phenyl)-pyrrolidin-1-yl]-(1-cyclobutanecarbonyl-piperidin-4-yl)-methanone;
[(3RS,4SR)-3-[(SR)-1-(5-chloro-pyridin-2-yloxy)-ethyl]-4-(3,4-dichloro-phenyl)-pyrrolidin-3-yl]-ethoxy}-nicotinonitrile;
[(3RS,4SR)-3-[(SR)-1-(5-chloro-pyridin-2-yloxy)-ethyl]-4-(3,4-dichloro-phenyl)-pyrrolidin-1-yl]-(1-isobutyl-piperidin-4-yl)-methanone;
4-[(3RS,4SR)-3-[(SR)-1-(5-cyano-pyridin-2-yloxy)-ethyl]-4-(3,4-dichloro-phenyl)-pyrrolidine-1-carbonyl]-piperidine-1-carboxylic acid tert-butyl ester;
6-{(SR)-1-[(3RS,4SR)-1-(1-cyclopropanecarbonyl-piperidine-4-carbonyl)-4-(3,4-dichloro-phenyl)-pyrrolidin-3-yl]-ethoxy}-nicotinonitrile;
6-((SR)-1-{(3RS,4SR)-4-(3,4-dichloro-phenyl)-1-[1-(1-methyl-cyclopropanecarbonyl)-piperidine-4-carbonyl]-pyrrolidin-3-yl}-ethoxy)-nicotinonitrile;
6-{(SR)-1-[(3RS,4SR)-1-[1-(1-amino-cyclopropanecarbonyl)-piperidine-4-carbonyl]-4-(3,4-dichloro-phenyl)-pyrrolidin-3-yl]-ethoxy}-nicotinonitrile; and
6-{(SR)-1-[(3RS,4SR)-1-(1-cyclobutanecarbonyl-piperidine-4-carbonyl)-4-(3,4-dichloro-phenyl)-pyrrolidin-3-yl]-ethoxy}-nicotinonitrile.

8. A compound of claim 6, wherein the compounds are
6-((SR)-1-{(3RS,4SR)-4-(3,4-dichloro-phenyl)-1-[1-(3-oxo-cyclobutanecarbonyl)-piperidine-4-carbonyl]-pyrrolidin-3-yl}-ethoxy)-nicotinonitrile;
6-{(SR)-1-[(3RS,4SR)-4-(3,4-dichloro-phenyl)-1-(1-propionyl-piperidine-4-carbonyl)-pyrrolidin-3-yl]-ethoxy}-nicotinonitrile;
6-{(SR)-1-[(3RS,4SR)-1-[1-(2-cyano-acetyl)-piperidine-4-carbonyl]-4-(3,4-dichloro-phenyl)-pyrrolidin-3-yl]-ethoxy}-nicotinonitrile;
6-((SR)-1-{(3RS,4SR)-4-(3,4-dichloro-phenyl)-1-[1-(2-methoxy-acetyl)-piperidine-4-carbonyl]-pyrrolidin-3-yl}-ethoxy)-nicotinonitrile;

1-(4-{(3SR,4RS)-3-(3,4-dichloro-phenyl)-4-[(SR)-1-(5-trifluoromethyl-pyridin-2-yloxy)-ethyl]-pyrrolidine-1-carbonyl}-piperidin-1-yl)-ethanone;

6-((SR)-1-{(3RS,4SR)-4-(3,4-dichloro-phenyl)-1-[1-(1-methyl-cyclopropanecarbonyl)-piperidine-4-carbonyl]-pyrrolidin-3-yl}-ethoxy)-nicotinonitrile;

[(3RS,4SR)-3-[(SR)-1-(5-chloro-pyridin-2-yloxy)-ethyl]-4-(2,4-difluoro-phenyl)-pyrrolidin-1-yl]-[1-(1-methyl-cyclopropanecarbonyl)-piperidin-4-yl]-methanone;

{(3S,4R)-3-(4-chloro-phenyl)-4-[(S)-1-(5-chloro-pyridin-2-yloxy)-ethyl]-pyrrolidin-1-yl}-[1-(1-methyl-cyclopropanecarbonyl)-piperidin-4-yl]-methanone; and {(3S,4R)-3-(4-chloro-3-fluoro-phenyl)-4-[(S)-1-(5-chloro-pyridin-2-yloxy)-ethyl]-pyrrolidin-1-yl}-[1-(1-methyl-cyclopropanecarbonyl)-piperidin-4-yl]-methanone.

9. A compound of claim 3, wherein X is —O—.

10. A compound of claim 9, wherein the compound is {(3SR,4RS)-3-(3,4-dichloro-phenyl)-4-[(SR)-1-(5-trifluoromethyl-pyridin-2-yloxy)-ethyl]-pyrrolidin-1-yl}-(tetrahydro-pyran-4-yl)-methanone.

11. A pharmaceutical composition comprising a compound of formula I

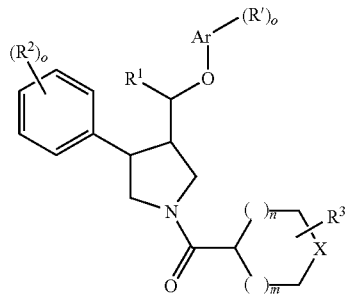

wherein
$R^1$ is hydrogen or lower alkyl;
each $R^2$ is independently halogen, CN, lower alkyl, or lower alkyl substituted by halogen;
Ar is aryl or heteroaryl;
R' is hydrogen, lower alkyl, halogen, cyano or lower alkyl substituted by halogen;
$R^3$ is hydrogen, lower alkyl or hydroxy;
X is —CH($R^4$)—, —N($R^{4'}$)— or —O—;
$R^4$ is hydrogen, hydroxy, =O, lower alkyl, lower alkynyl, —S(O)$_2$-lower alkyl, —C(O)-lower alkyl, —C(O)CH$_2$O-lower alkyl, —CH$_2$CN, —C(O)CH$_2$CN,
  —C(O)-cycloalkyl wherein the cycloalkyl group is optionally substituted by cyano, lower alkyl, one or two halogen atoms, =O or amino, or is —C(O)O-lower alkyl, —NH-lower alkyl, —NRC(O)O-lower alkyl, —NRC(O)-lower alkyl or —CH$_2$O-lower alkyl;
$R^{4'}$ is hydrogen, lower alkyl, —S(O)$_2$-lower alkyl, —C(O)-lower alkyl, —C(O)CH$_2$—O-lower alkyl, —CH$_2$CN, —C(O)CN, —C(O)CH$_2$CN,
  —C(O)-cycloalkyl wherein the cycloalkyl group is optionally substituted by cyano, lower alkyl, one or two halogen atoms, =O or amino, or is —C(O)O-lower alkyl or —CH$_2$O-lower alkyl;
R is hydrogen or lower alkyl; or
$R^3$ and $R^4$ together with the carbon atoms to which they are attached form a five or six-membered non aromatic ring or
$R^3$ and $R^{4'}$ together with the nitrogen and carbon atoms to which they are attached form a five or six-membered non aromatic ring;
n is 0 or 1;
m is 0, 1, or 2 when n is 0; or
m is 0 or 1 when n is 1; and
o is 0, 1, 2 or 3;
or a pharmaceutically active salt, racemic mixture, enantiomer, optical isomer or tautomeric form thereof and a pharmaceutically acceptable carrier.

* * * * *